`US008974537B2`

(12) United States Patent
Dreyfuss

(10) Patent No.: US 8,974,537 B2
(45) Date of Patent: *Mar. 10, 2015

(54) METHOD FOR AN ARTICULATING HUMERAL HEAD PROSTHESIS

(75) Inventor: Peter J. Dreyfuss, Naples, FL (US)

(73) Assignee: Arthrex, Inc., Naples, FL (US)

( * ) Notice: Subject to any disclaimer, the term of this patent is extended or adjusted under 35 U.S.C. 154(b) by 148 days.

This patent is subject to a terminal disclaimer.

(21) Appl. No.: 12/694,344

(22) Filed: Jan. 27, 2010

(65) Prior Publication Data
US 2010/0191340 A1    Jul. 29, 2010

Related U.S. Application Data

(63) Continuation-in-part of application No. 12/113,849, filed on May 1, 2008, now Pat. No. 8,591,592.

(60) Provisional application No. 60/915,280, filed on May 1, 2007.

(51) Int. Cl.
*A61F 2/40* (2006.01)
*A61B 17/88* (2006.01)
(Continued)

(52) U.S. Cl.
CPC ........... *A61F 2/4612* (2013.01); *A61B 17/1684* (2013.01); *A61F 2/4003* (2013.01); *A61B 17/1615* (2013.01); *A61B 17/29* (2013.01); *A61B 17/86* (2013.01); *A61B 2017/2932* (2013.01); *A61B 2017/305* (2013.01);
(Continued)

(58) Field of Classification Search
USPC .......... 623/14.12, 19.11–19.14, 23.42–23.48, 623/902; 606/81
See application file for complete search history.

(56) References Cited

U.S. PATENT DOCUMENTS 4,328,593 A * 5/1982 Sutter et al. ................ 623/23.42
4,484,570 A    11/1984 Sutter et al.
(Continued)

FOREIGN PATENT DOCUMENTS

DE   10 2004 042 502 A1   3/2006
WO        WO 01/22905 A1   4/2001

OTHER PUBLICATIONS

G. Cerulli, A. Caraffa, C. Senni, and S. Brué, "Tenica all-inside de ricostruzione del legamento crociato anteriore," *Chirurgia artroscopica dell'arto inferiore*, Capitolo G 7, pp. 1-4, Mattioli 1885 Editore, 2005, with English translation. The year of publication is sufficiently earlier than the effective U.S. filing date and any priority date so that the particular month of publication is not in issue. See MPEP 609.04(a).

(Continued)

*Primary Examiner* — Marcia Watkins
(74) *Attorney, Agent, or Firm* — Dickstein Shapiro LLP

(57) ABSTRACT

A humeral prosthesis includes a stem component and a humeral head component. The humeral head component has a configuration that is similar to the curvature of the humeral head to allow the head to reconstruct the anatomy of the damaged humerus. The stem component is threaded and cannulated and engages the humeral head component. The stem component is configured to be inserted within the humeral diaphyseal channel. When engaged the humeral head component and the stem component form an articulated joint allowing the humeral head component to articulate with respect to the stem component.

4 Claims, 28 Drawing Sheets

(51) Int. Cl.
*A61B 17/56* (2006.01)
*A61F 2/46* (2006.01)
*A61B 17/16* (2006.01)
*A61B 17/29* (2006.01)
*A61B 17/86* (2006.01)
*A61B 17/30* (2006.01)
*A61F 2/30* (2006.01)
*A61B 17/17* (2006.01)

(52) U.S. Cl.
CPC ............... *A61F 2002/30433* (2013.01); *A61F 2002/30507* (2013.01); *A61F 2002/30538* (2013.01); *A61F 2002/3054* (2013.01); *A61F 2002/30736* (2013.01); *A61F 2002/3085* (2013.01); *A61F 2002/30878* (2013.01); *A61F 2002/30886* (2013.01); *A61F 2002/30901* (2013.01); *A61F 2002/30902* (2013.01); *A61F 2002/4007* (2013.01); *A61F 2002/4622* (2013.01); *A61F 2002/4631* (2013.01); *A61F 2220/0025* (2013.01); *A61F 2220/0041* (2013.01); *A61F 2250/0006* (2013.01); *A61B 2017/1778* (2013.01); *Y10S 623/908* (2013.01)
USPC ............ 623/19.14; 623/908; 606/80; 606/96; 606/99

(56) References Cited

U.S. PATENT DOCUMENTS

| | | | |
|---|---|---|---|
| 5,100,405 | A | 3/1992 | McLaren |
| 5,800,551 | A | 9/1998 | Williamson et al. |
| 6,482,237 | B2 * | 11/2002 | Mosseri ..................... 623/22.12 |
| 6,716,234 | B2 | 4/2004 | Grafton et al. |
| 7,097,663 | B1 * | 8/2006 | Nicol et al. ................ 623/19.13 |
| 2002/0022889 | A1 | 2/2002 | Chibrac et al. |
| 2003/0014123 | A1 | 1/2003 | Copf et al. |
| 2003/0060887 | A1 * | 3/2003 | Ek .............................. 623/20.14 |
| 2003/0212402 | A1 * | 11/2003 | White et al. .................... 606/81 |
| 2004/0093031 | A1 | 5/2004 | Burkhart et al. |
| 2004/0193278 | A1 * | 9/2004 | Maroney et al. ........... 623/19.14 |
| 2005/0080455 | A1 | 4/2005 | Schmieding et al. |
| 2005/0159751 | A1 * | 7/2005 | Berthusen et al. ............... 606/80 |
| 2006/0085006 | A1 | 4/2006 | Ek et al. |
| 2006/0149370 | A1 | 7/2006 | Schmieding et al. |
| 2007/0282450 | A1 * | 12/2007 | Habermeyer et al. ...... 623/19.14 |
| 2010/0262144 | A1 * | 10/2010 | Kelman et al. .................. 606/62 |

OTHER PUBLICATIONS

G. Cerulli, A. Caraffa, C. Senni, and S. Brué, "All-Inside Technique for ACL Reconstructive," *6° Corso Internazionale Ortopedia, Biomeccanica, Riabilitazione Sportive*, Abstracts Book, Assisi, Nov. 22-24, 2002, pp. 45-46.

* cited by examiner

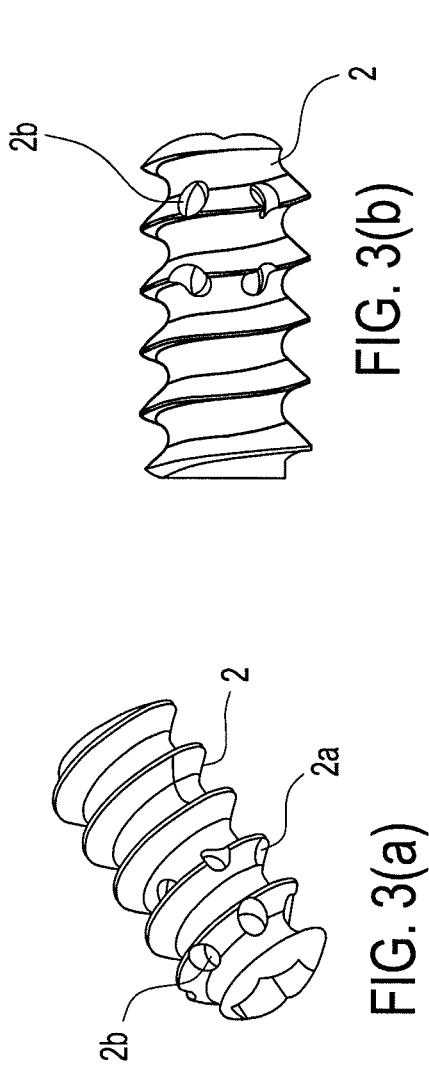
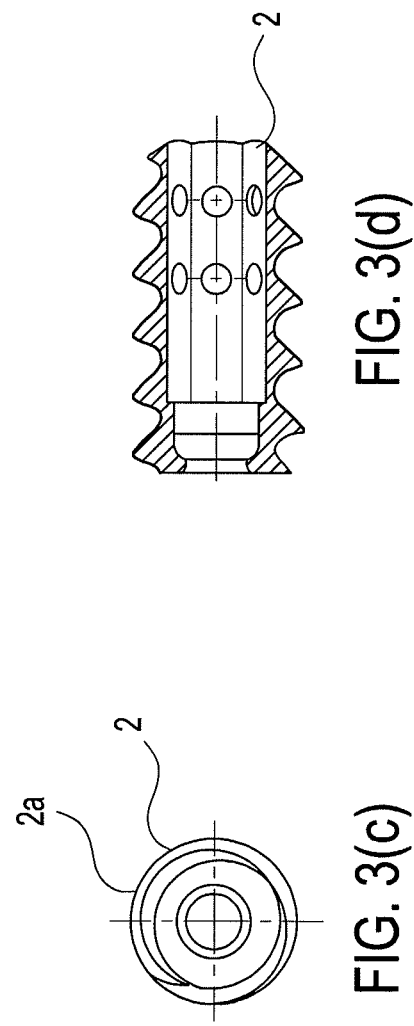

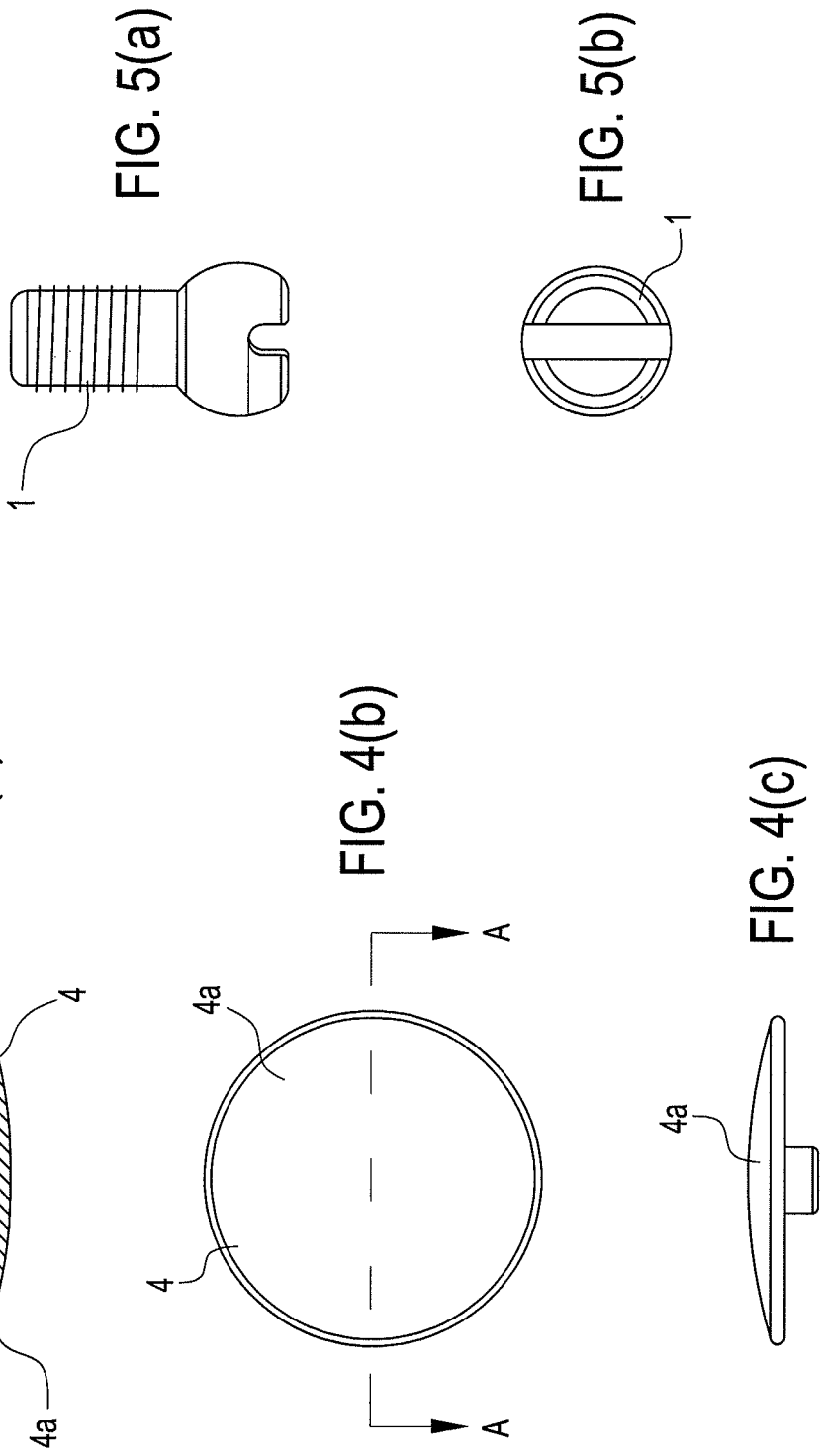

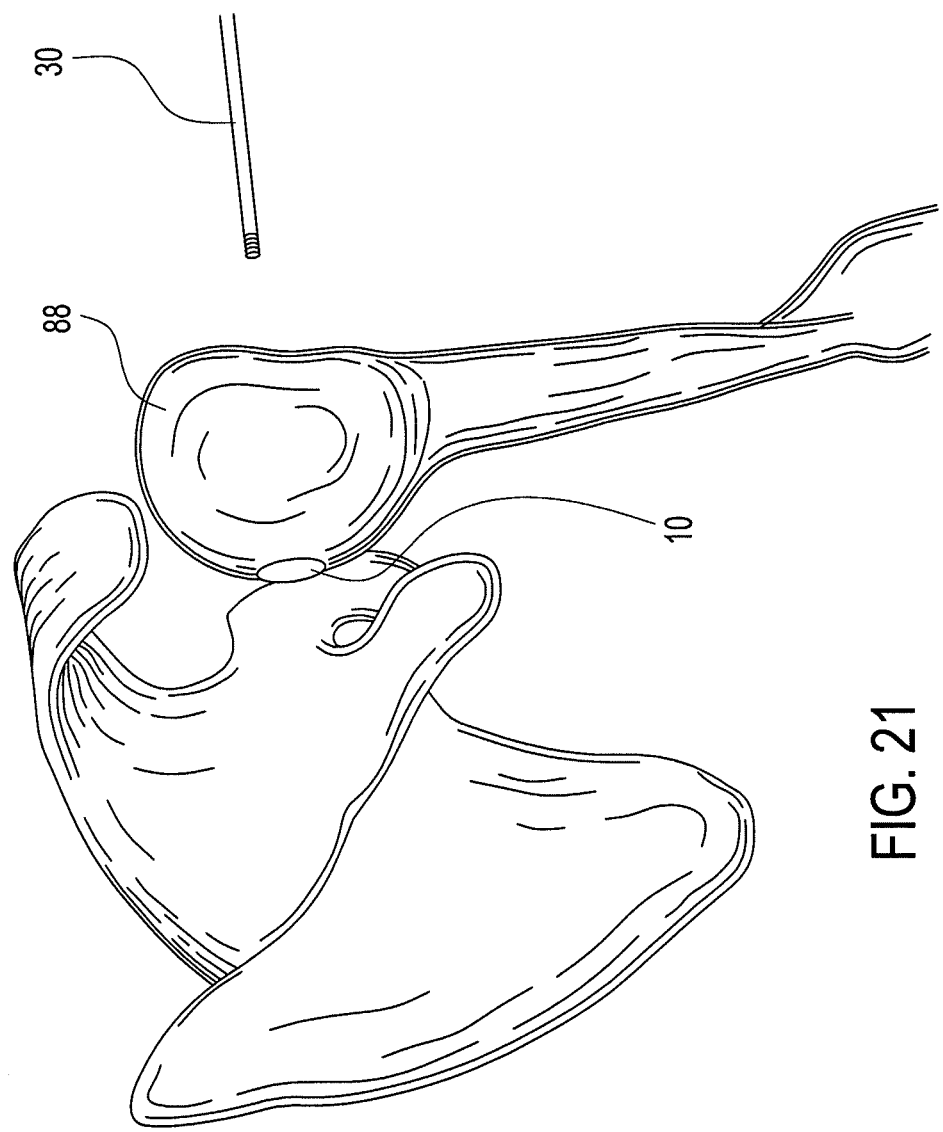

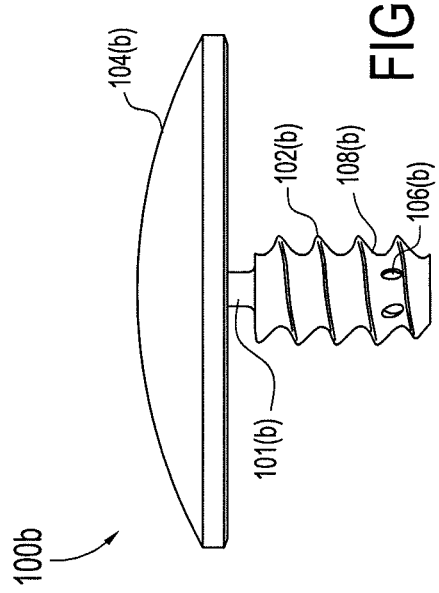
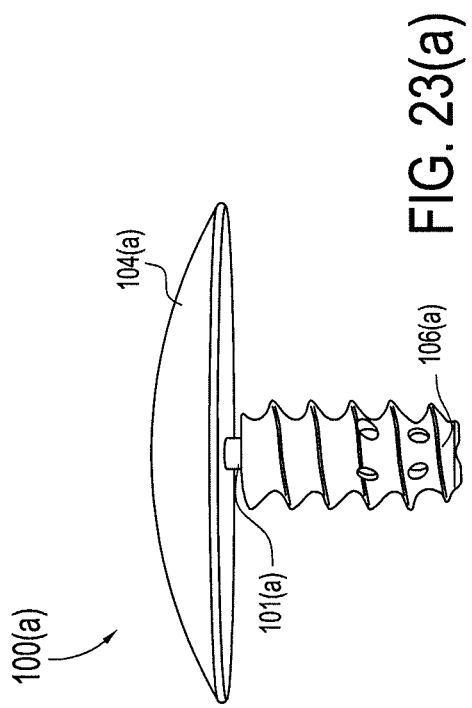
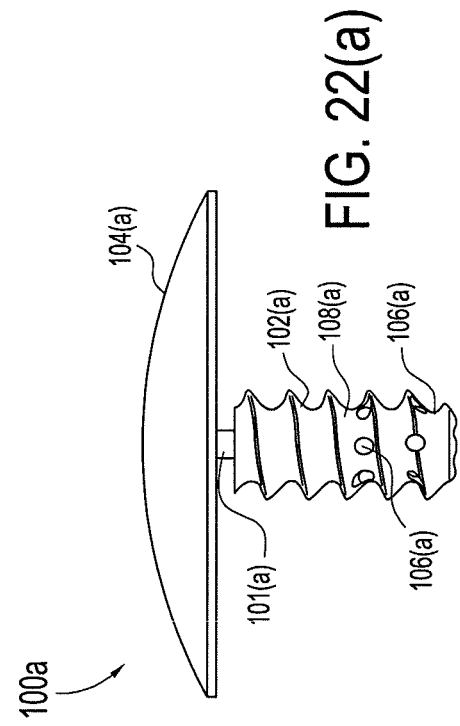

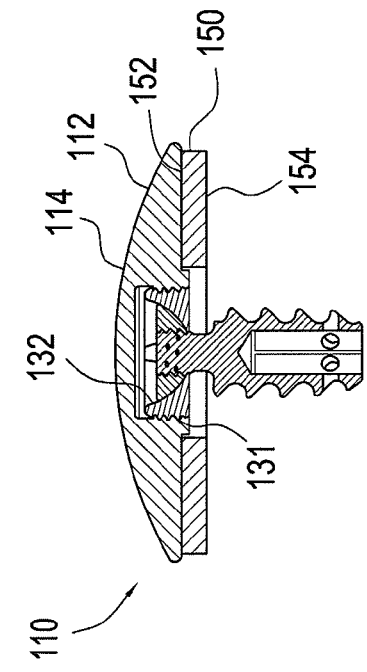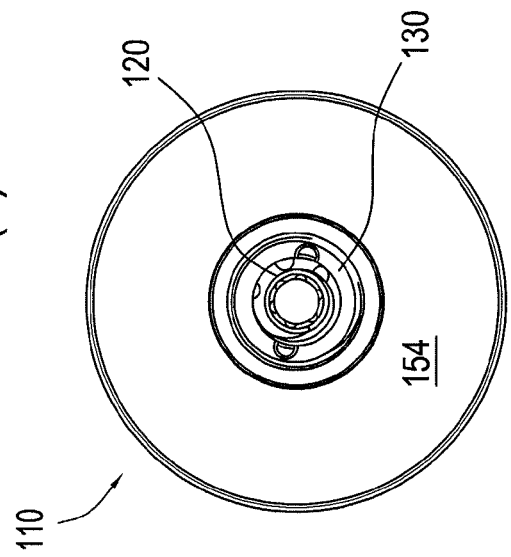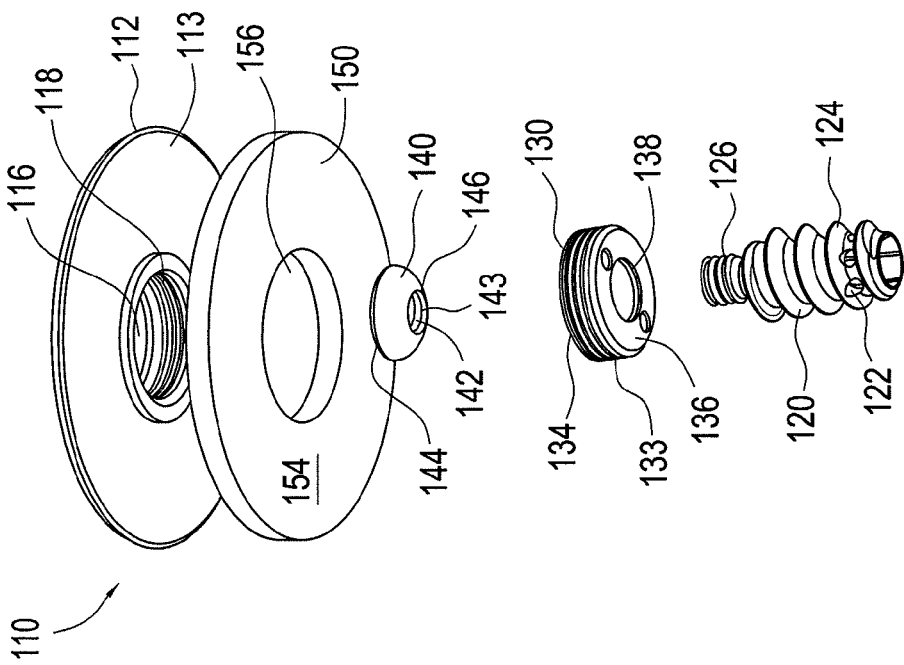

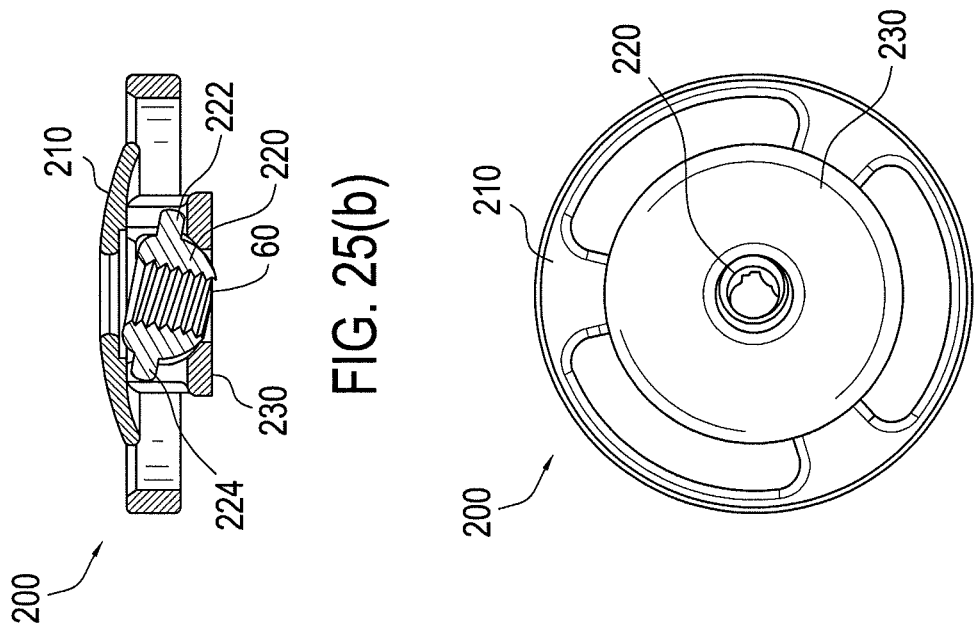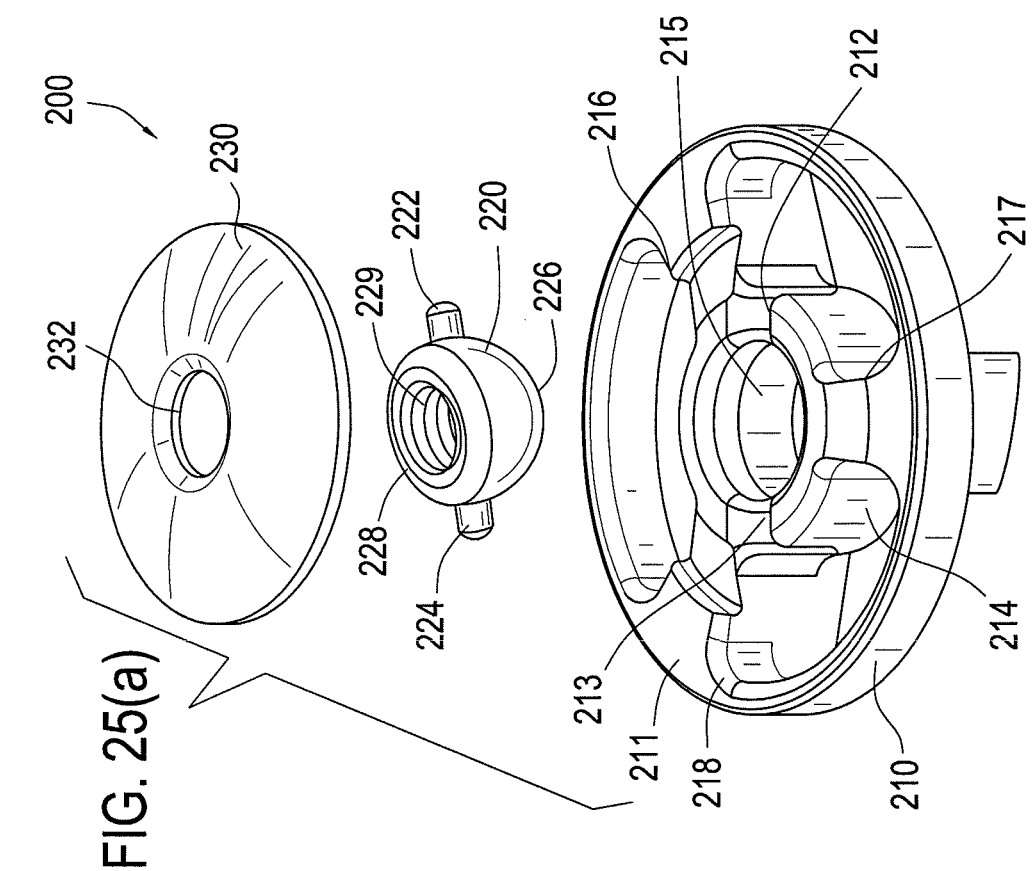

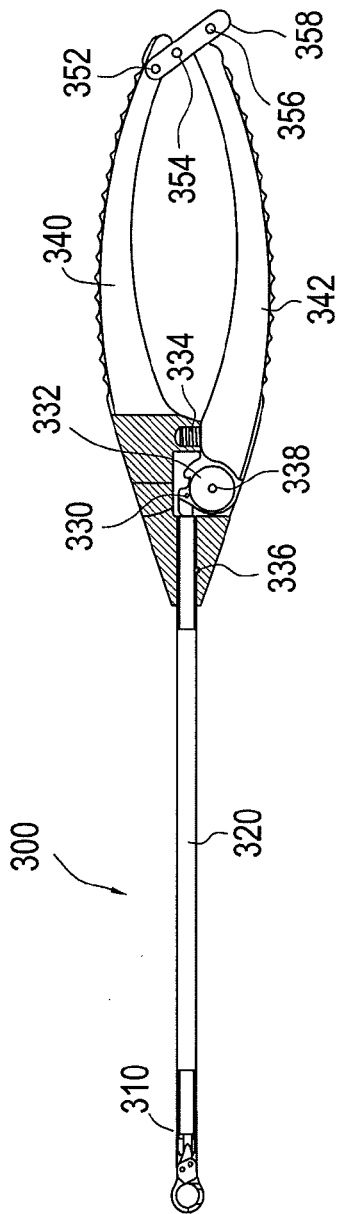
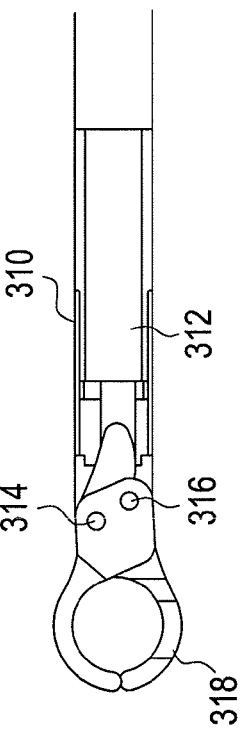
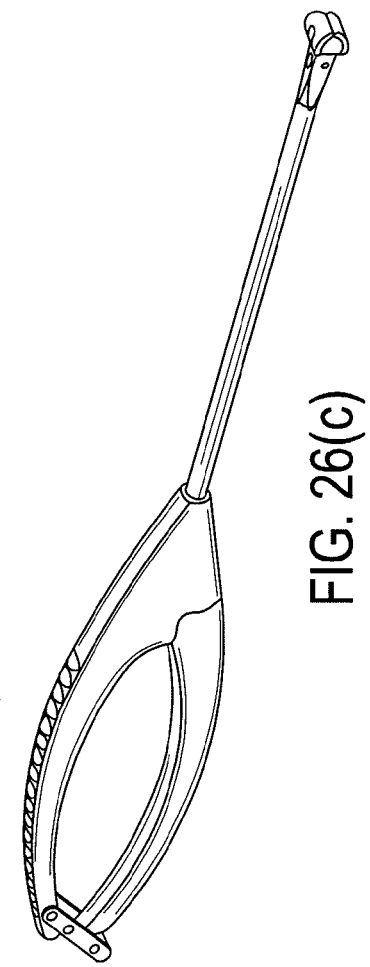
FIG. 26(a)
FIG. 26(b)
FIG. 26(c)

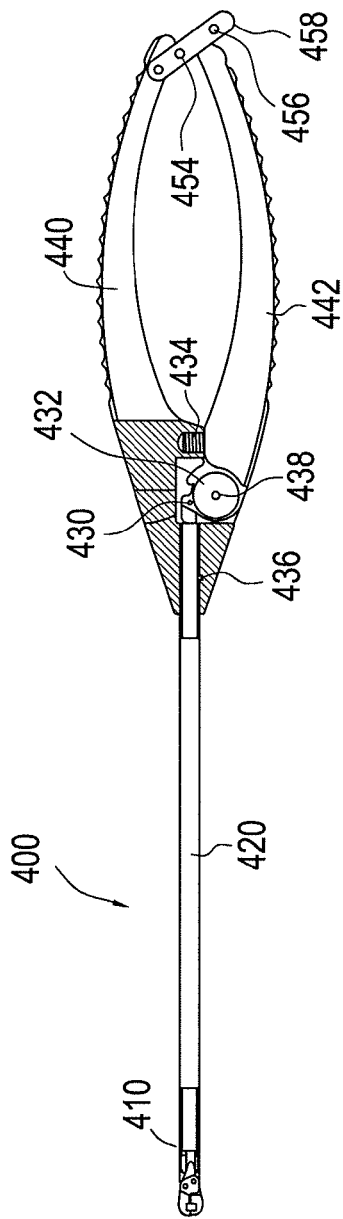
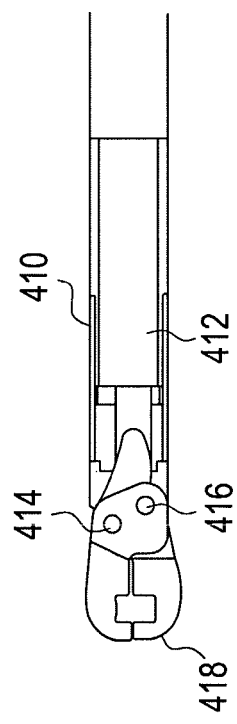
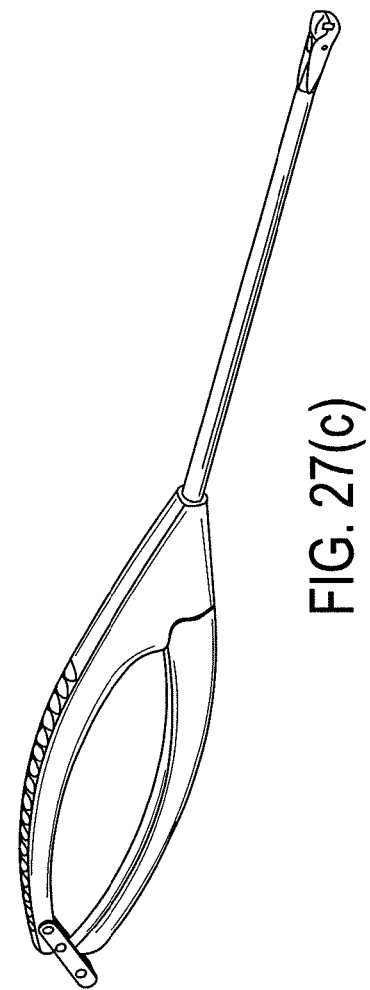
FIG. 27(a)
FIG. 27(b)
FIG. 27(c)

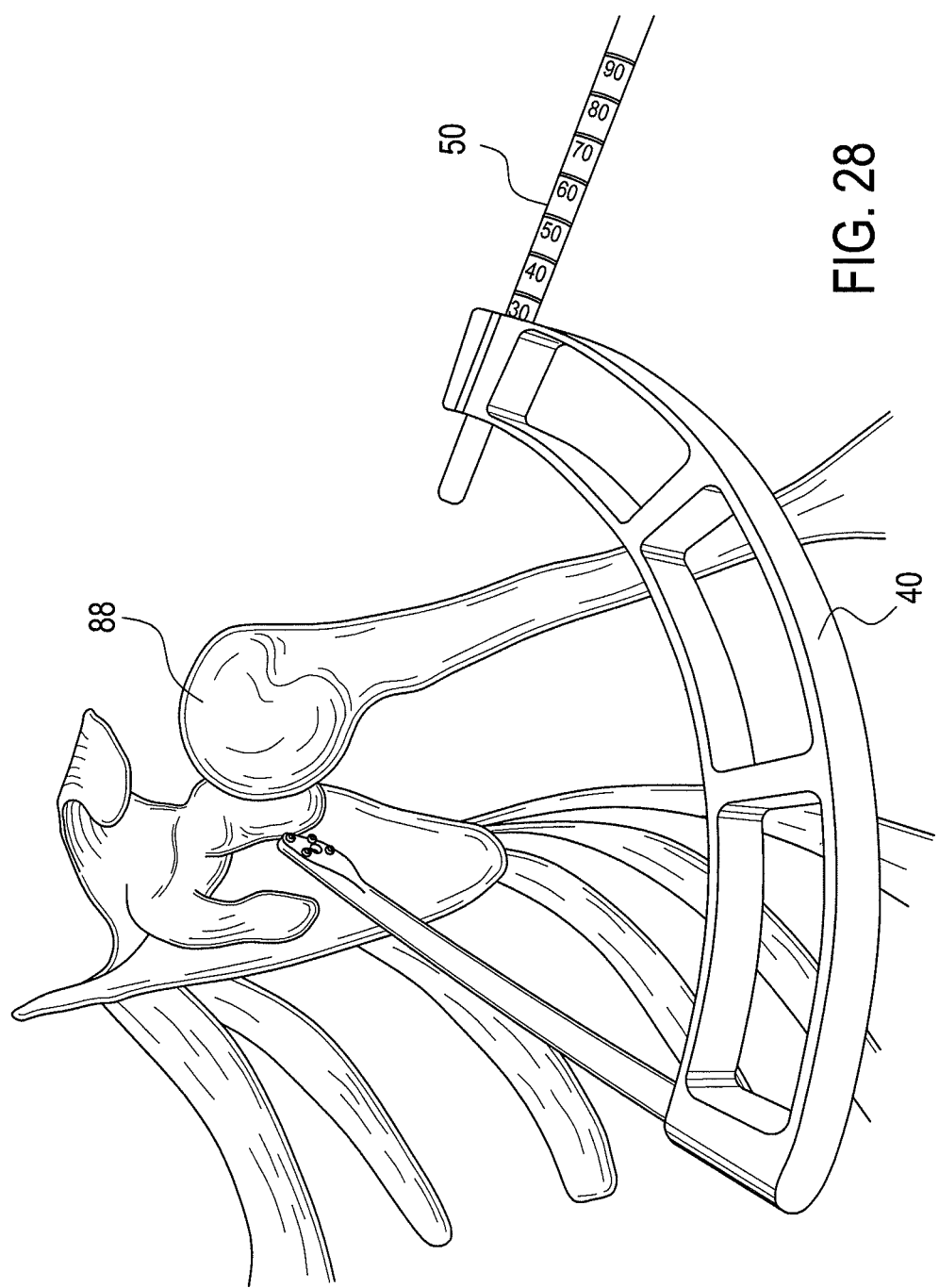

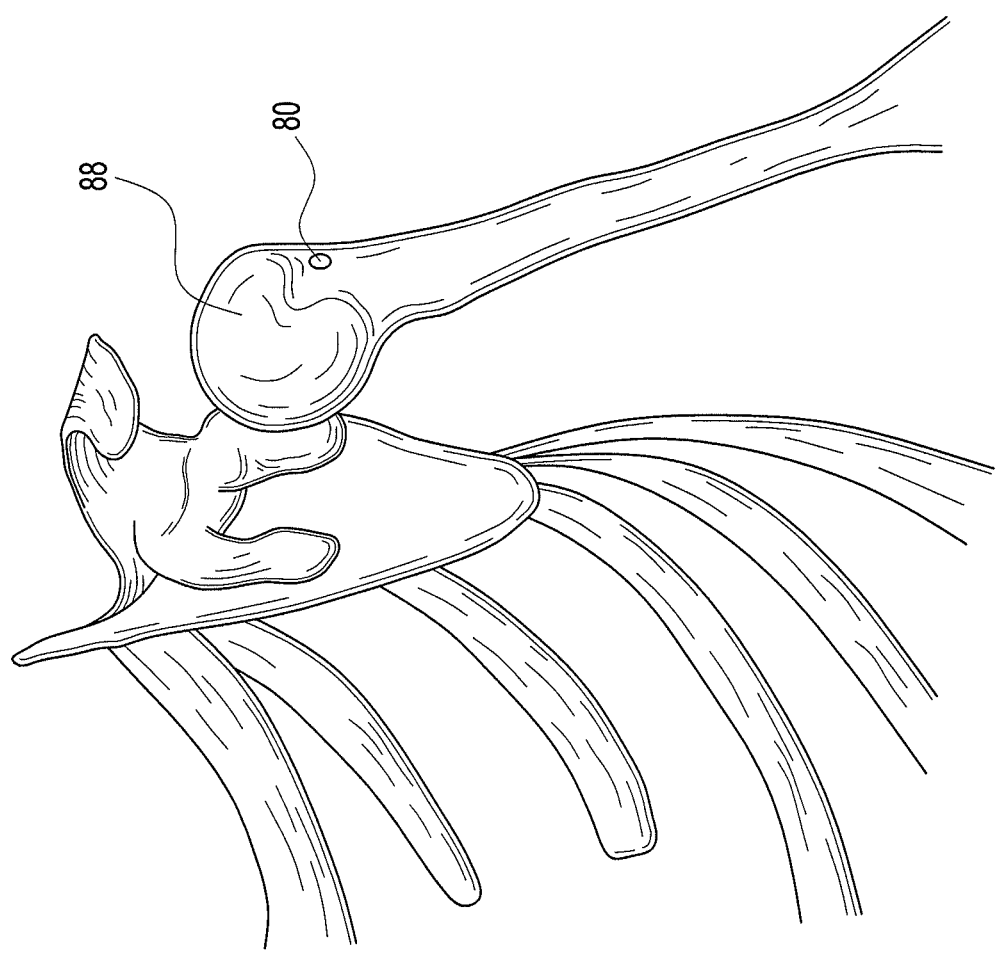

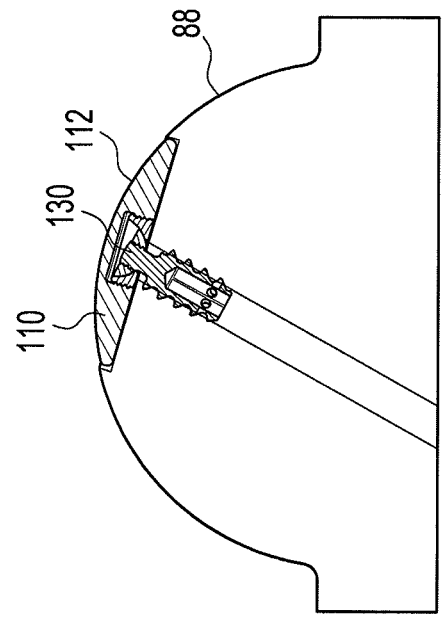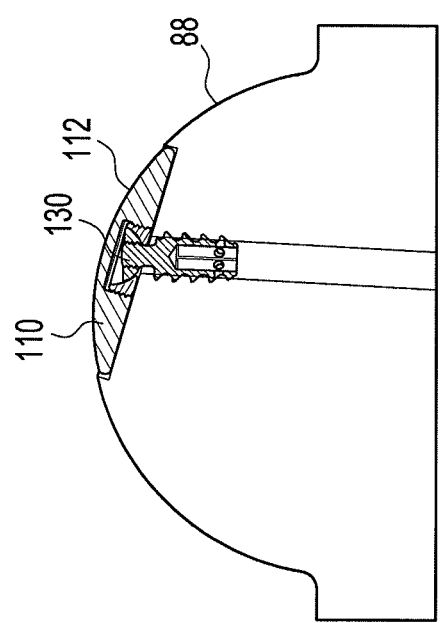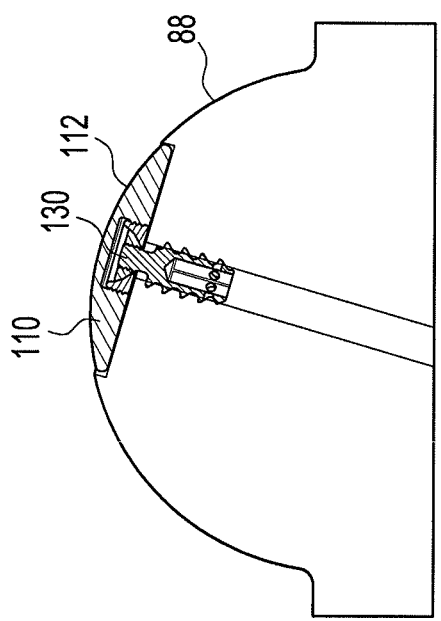

METHOD FOR AN ARTICULATING HUMERAL HEAD PROSTHESIS

CROSS-REFERENCE TO RELATED APPLICATIONS

This application is a continuation-in-part of U.S. application Ser. No. 12/113,849, filed on May 1, 2008 now U.S. Pat. No. 8,591,592, which claims the benefit of U.S. Provisional Application Ser. No. 60/915,280, filed May 1, 2007, the entire disclosures of which are incorporated by reference herein.

FIELD OF THE INVENTION

The present invention relates to surgical reconstitution of anatomical structures and, in particular, to prosthetic replacement of such structures.

BACKGROUND OF THE INVENTION

Instability and other maladies of human joints, such as arthrosis or fracture, can be sufficiently acute that prosthetic replacement of compromised joint features may be indicated. For example, in shoulder reconstruction, the humeral head may be replaced by first resecting the humeral head from the humerus and then installing a humeral prosthetic at the resection.

Various prostheses have been designed to mimic the portion of the joint or joint region being replaced. A shoulder prostheses, for example, includes a stem to be anchored in the humeral canal and a hemispherical head to be positioned within the glenoid cavity of the scapula. The more-recently devised modular shoulder prostheses generally are modular systems that allow flexibility with respect to either the tilt angle or the radial offset between the head and stem.

SUMMARY OF THE INVENTION

The present invention provides a novel prosthetic assembly for prosthetic and surgical methods for reconstitution of a joint, with special applications to the shoulder joint. The prosthetic assembly includes a partial humeral head component.

The present invention also provides a method of conducting surgery by providing a prosthetic assembly comprising a partial humeral head component fixed within a socket formed in the humerus.

The present invention also includes a humeral head cap used in conjunction with a humeral head reamer (preferably a retrograde reamer) that resurfaces an articular surface in a retrograde manner without direct exposure to the surface. In this manner, slight errors in placement of the initial drill pin are corrected by the articulation of the reamer and the humeral head cap.

The present invention also includes a prosthetic for replacing a portion of a bone that includes a spherical head and a post having a proximal end and a distal end. The spherical head has a convex surface suitable to be introduced within a joint cavity, a concave surface that contacts the bone and an articulating coupling element for attaching the proximal end of the post to the spherical head. The spherical head is contoured to engage a complementary articular surface.

The post is a cannulated member at least partially insertable within a diaphyseal channel of the bone and is removably attached to the spherical head. The coupling element of the prosthetic includes a socket and an articulating part that interacts with the socket to form an articulating ball and socket joint, so that the spherical head can articulate in all directions in relationship to the post.

The present invention also includes a humeral prosthetic component, that includes a cannulated screw having a proximal end and a distal end, where at least a portion of the distal end is configured to be at least partially insertable within the humeral diaphyseal channel. The component includes a head having a convex surface suitable to be introduced within a joint cavity and an articulating part.

The articulating part of the component is configured to attach the cannulated screw to the head to form an articulated joint, wherein the articulating joint allows the head to articulate in relationship to the screw.

The present invention also includes a surgical component that has a spherical body suitable to be introduced within a joint cavity. The body also has at least one cutting edge and an articulating coupling element for attaching the body to a driver. The body of the component may include three cutting edges and the articulating coupling element allows the body to articulate in relationship to an attached driver.

The present invention also includes a method of shoulder repair, the method includes the steps of: providing a humeral prosthetic and providing the humeral prosthetic within a patient's humerus. The humeral prosthetic includes a post having a proximal end and a distal end, at least a portion of the distal end of the post being configured to be insertable within the humeral diaphyseal channel and a head secured to the proximal end of the post, the head having a convex surface suitable to be introduced within a joint cavity wherein an articulating coupling element attaches the post to the head.

The method further includes resecting a portion of the humeral head at a defect location, preparing a socket in the defect location of the humerus and providing the head at the defect location so that the head is flush with the humeral contour. Wherein the step of preparing the socket is done using a reamer that comprises an articulating joint for connecting to a reamer driver.

Furthermore, the reamer articulates in relationship to the reamer driver and the head articulates in relationship to the post.

These and other features and advantages of the invention will be more apparent from the following detailed description that is provided in connection with the accompanying drawings and illustrated exemplary embodiments of the invention.

BRIEF DESCRIPTION OF THE DRAWINGS

FIGS. 1-5 illustrate various views of a partial humeral head prosthesis according to a first embodiment of the present invention;

FIGS. 15-21 illustrate steps of a method of replacing a portion of the humeral head with the partial humeral head prosthesis of the present invention;

FIGS. 22 and 23 illustrate various views of a partial humeral head prosthesis according to a second embodiment of the present invention;

FIG. 24 illustrates various views of a humeral head prosthesis according to a third embodiment;

FIG. 25 illustrates various views of a humeral head prosthesis reamer according to a third embodiment;

FIG. 26 illustrates various views of a reamer grasper instrument according to an exemplary embodiment;

FIG. 27 illustrates various views of an implant grasper instrument according to an exemplary embodiment;

FIGS. 28-34 illustrate steps of a method of replacing a portion of the humeral head with the humeral head prosthesis according to a third embodiment; and FIG. 35 illustrates various views of a humeral head prosthesis seated on a humeral head.

DETAILED DESCRIPTION OF THE PREFERRED EMBODIMENTS

Figure 2:
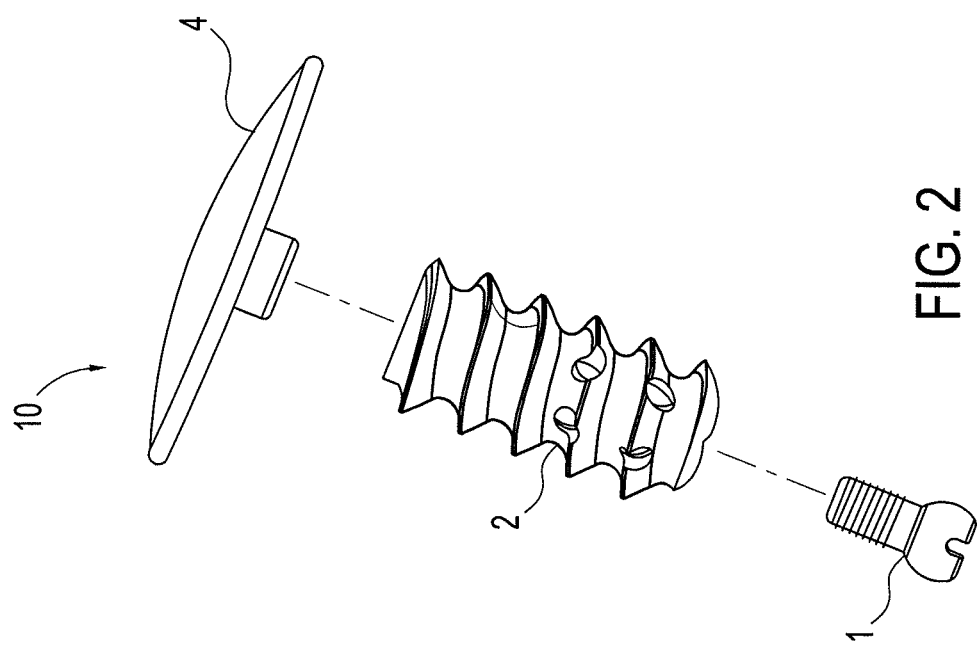
Figure 1:
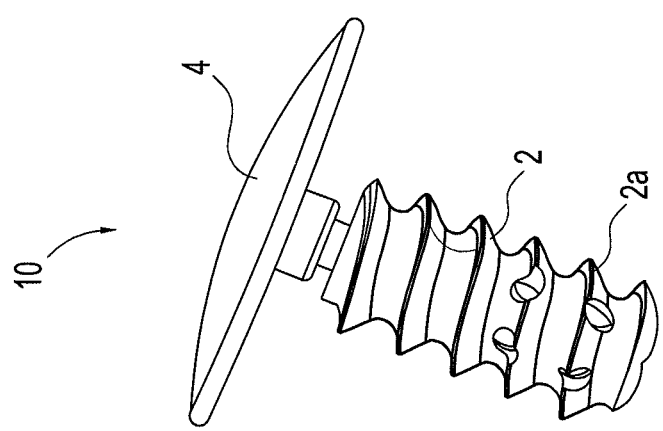

The invention provides prosthetic assembly for prosthetic and surgical methods for reconstitution of a joint, with special applications to the shoulder joint. As detailed below, the prosthetic assembly includes a partial humeral head prosthesis component that is configured to be inserted in a socket formed in the humerus.

Referring now to the drawings, where like elements are designated by like reference numerals, FIGS. 1-5 illustrate a first exemplary embodiment of partial humeral head prosthesis 10 of the present invention. Partial humeral head prosthesis 10 comprises a partial humeral head prosthesis cap 4 securely engaged to a partial implant or screw 2 by shoulder post 1. FIGS. 3(a)-(e) illustrate additional views of the partial humeral head prosthesis implant or screw 2. FIGS. 4(a)-(c) illustrate additional views of the partial humeral head prosthesis cap 4. FIGS. 5(a)-(b) illustrate additional views of the shoulder post or pin 1.

As shown in the drawings, prosthesis cap 4 of the partial humeral head prosthesis 10 is configured to allow replacement of a portion of the humeral head with the prosthesis cap. In an exemplary embodiment, and as shown in FIGS. 4(a)-(c), partial humeral head prosthesis cap 4 has a convex configuration (a partial eclipse-type configuration), which is similar to the curvature of the humeral head to allow the prosthesis cap 4 to reconstruct the anatomy of the damaged humeral head. As described below, convex outer surface 4a (FIGS. 4(a)-4(c)) of the prosthesis cap 4 will permit both the full anatomical reconstruction of the humeral head and the introduction of the convex surface within the glenoid cavity. The concave, inner surface 4b (FIG. 4(a)) abuts the surface of the damaged articular bone to be replaced (i.e., portion of the humerus) and permits containment of any fractured, damaged humeral head. The dimension and measurements of the partial humeral head prosthesis cap 4 are a function of the patient's anatomy.

The partial humeral head prosthesis implant or screw 2 shown in FIGS. 3(a)-(e) is engaged to the prosthesis cap 4 through shoulder post or pin 1 shown in FIGS. 5(a)-(b). As detailed in FIGS. 3(a)-(e), implant or screw 2 is provided with threads 2a to allow the insertion and subsequent fixation of the screw (with prosthesis cap 4 attached thereto) into the humerus diaphyseal channel. A plurality of fenestrations or holes 2b formed through the body of the screw 2 permit the passage of any fixing material (such as acrylic cement, for example) through the walls of the screw 2, to increase the fixation of the device within the diaphyseal channel.

Partial humeral head prosthesis 10 may be manufactured from titanium alloy or other metallic materials. The partial humeral head prosthesis cap 4 preferably is manufactured from materials similar to those of the screw 2 and pin 1.

Figure 7:
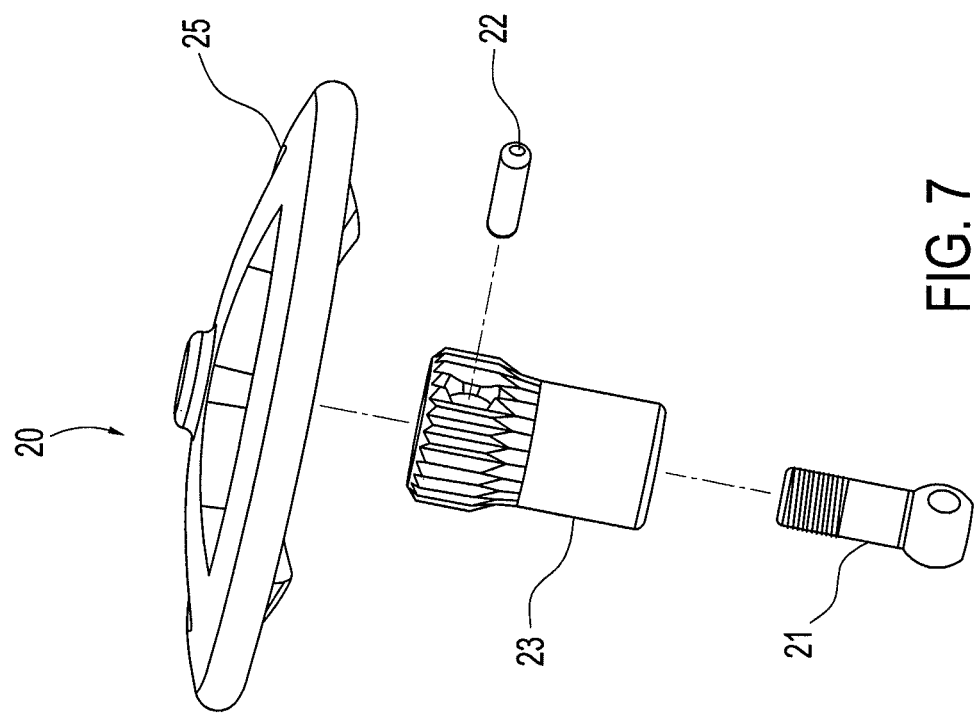
FIGS. 6-8 illustrate various views of a partial humeral head prosthesis duster of the present invention.
Figure 6:
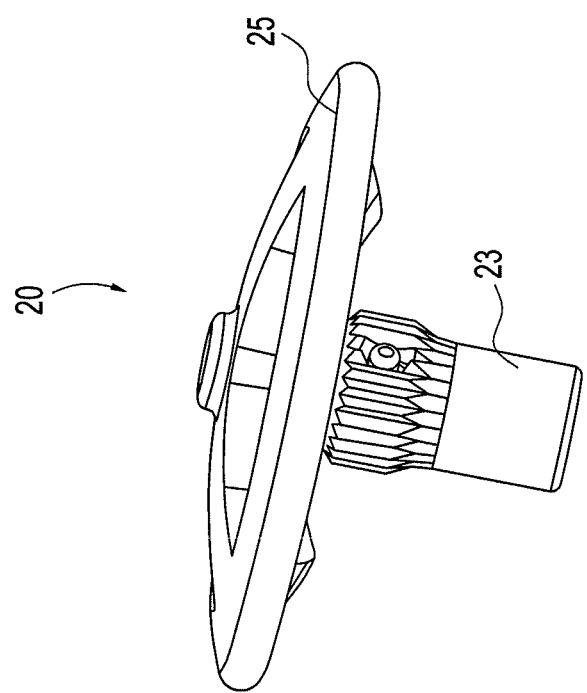
Figure 8:
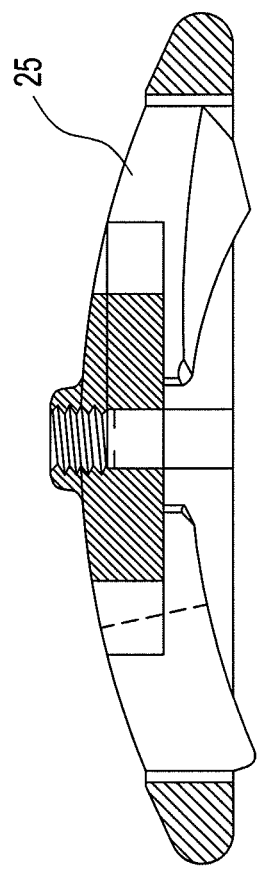

FIGS. 6-8 illustrate various views of partial humeral head prosthesis duster 20 of the present invention. As shown in the drawings, the partial humeral head prosthesis duster 20 comprises duster cap 25 securely engaging reamer 23 through ball post 21 and pin 22.

Figure 9:
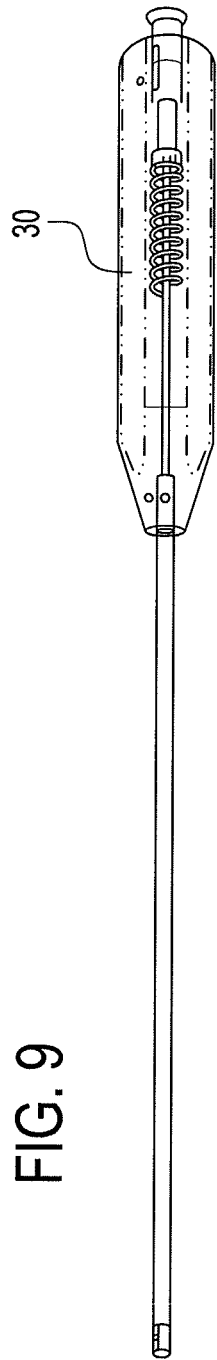
FIGS. 9-11 illustrate various views of a driver for the partial humeral head prosthesis of the present invention.
Figure 10:
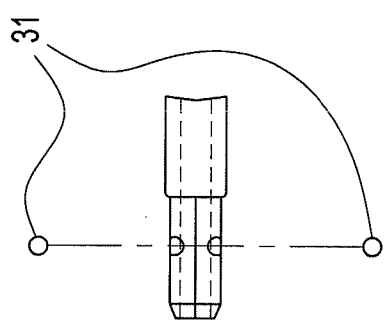
Figure 11:
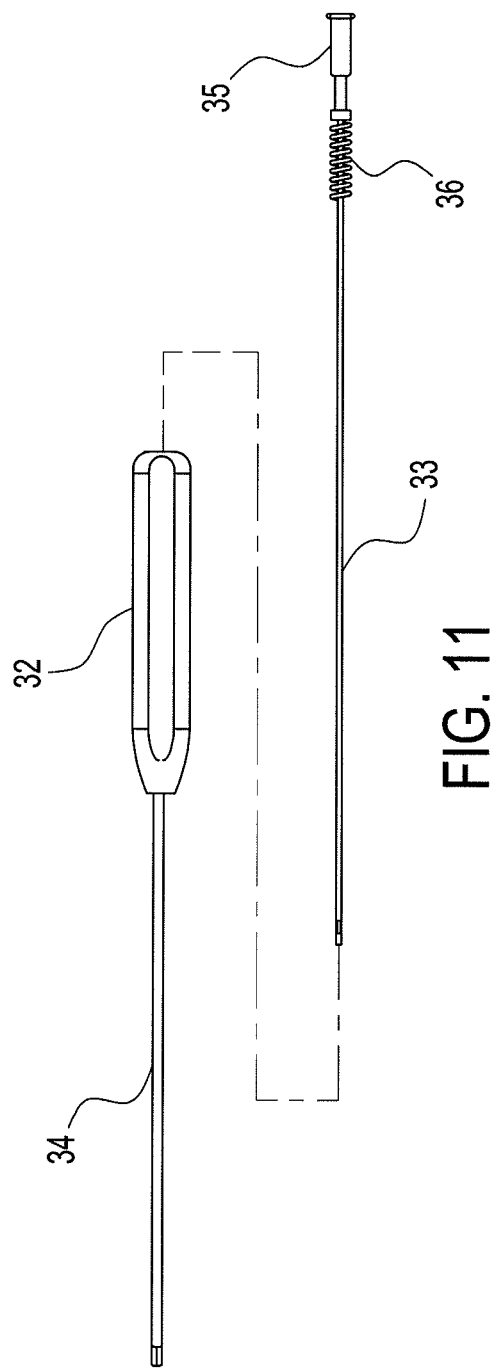

FIGS. 9-11 illustrate a driver 30 for the partial humeral head prosthesis 10 of the present invention. Driver 30 comprises an inner rod 33 disposed within a cannulated rod 34, and a handle 32. Driver 30 also comprises a spring driver 36, a spring plug 35 and ball bearings 31.

Figure 12:
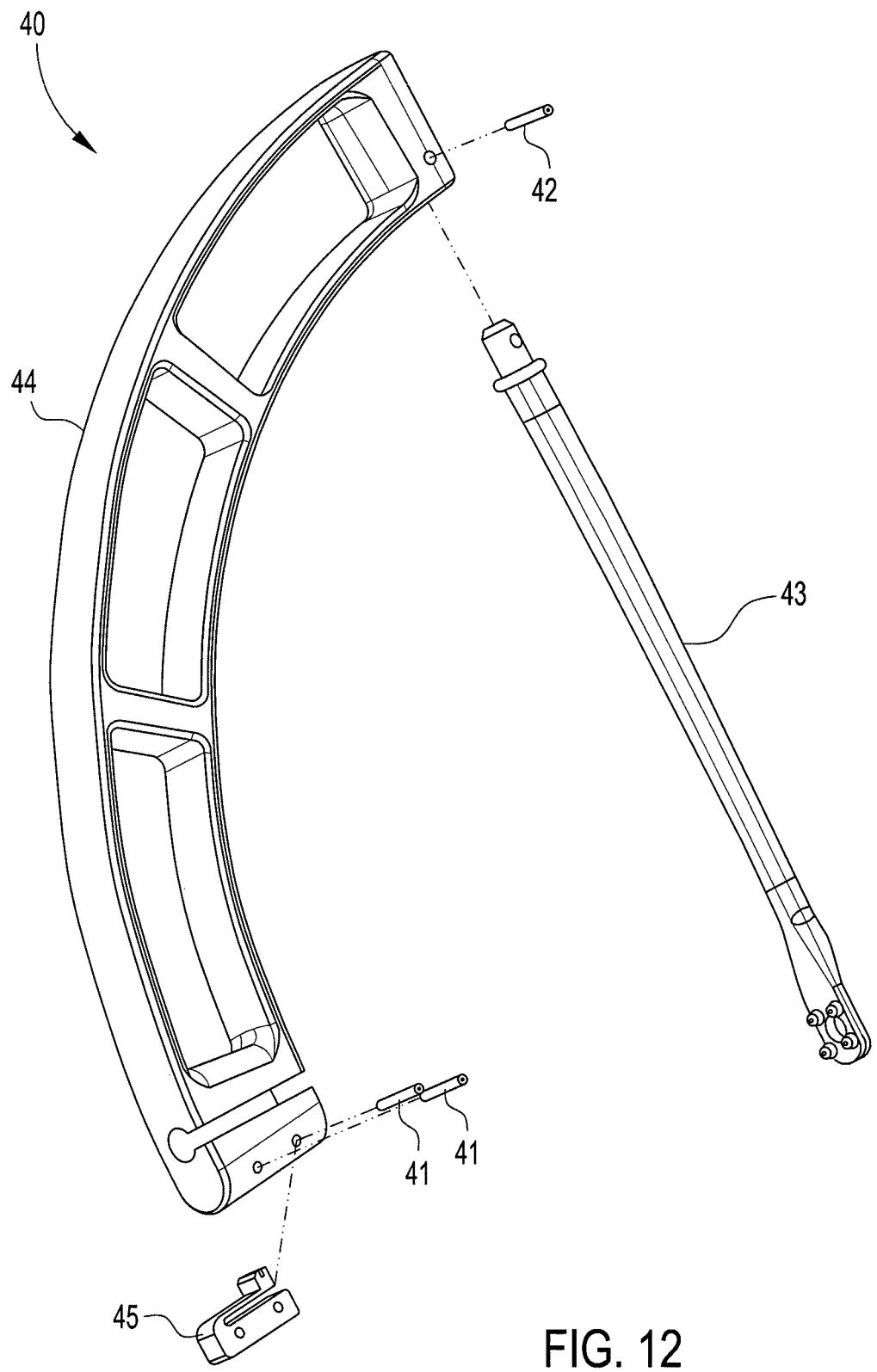
FIG. 12 illustrates a drill guide for installing the partial humeral head prosthesis of the present invention.

FIG. 12 illustrates a drill guide 40 for the partial humeral head prosthesis 10 of the present invention. Drill guide 40 comprises a handle frame 44, a guide arm 43, pins 41, 42 and spring latch 45.

Figure 13:
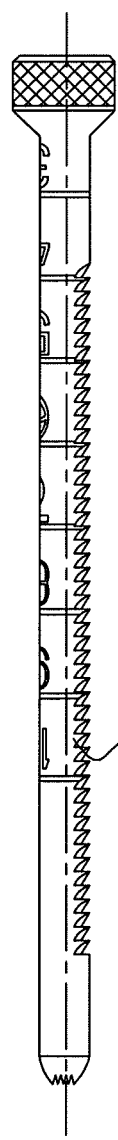
FIG. 13 illustrates a drill sleeve for use with the drill guide of the present invention.
Figure 14:
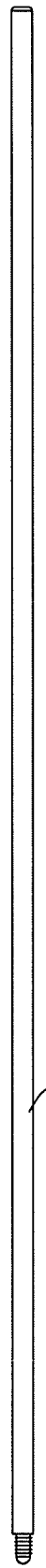
FIG. 14 illustrates various views of a pin for retrograde drilling of the duster of FIGS. 6-8 in connection with the present invention.

FIG. 13 shows a drill sleeve 50 for use with the drill guide 40 of FIG. 12 in connection with the present invention. FIG. 14 illustrates a threaded pin 60 for attachment to, and retrograde drilling of, duster 20 in connection with the present invention, as described in the technique below.

The present invention also provides a method of conducting arthroscopic surgery by fixating the humeral head prosthesis 10 of the present invention within a socket in the humerus. Preparation for an exemplary surgical technique relies upon radiographic film, surgical templates, and trial implants to determine and select the appropriate combination of end cap 4, screw 2 and pin 1 that make up partial humeral head prosthesis (implant) 10 to meet the patient's anatomical requirements. The remaining fractured/damaged humerus is resected using appropriate instrumentation designed specifically for the implant system.

Figure 15:
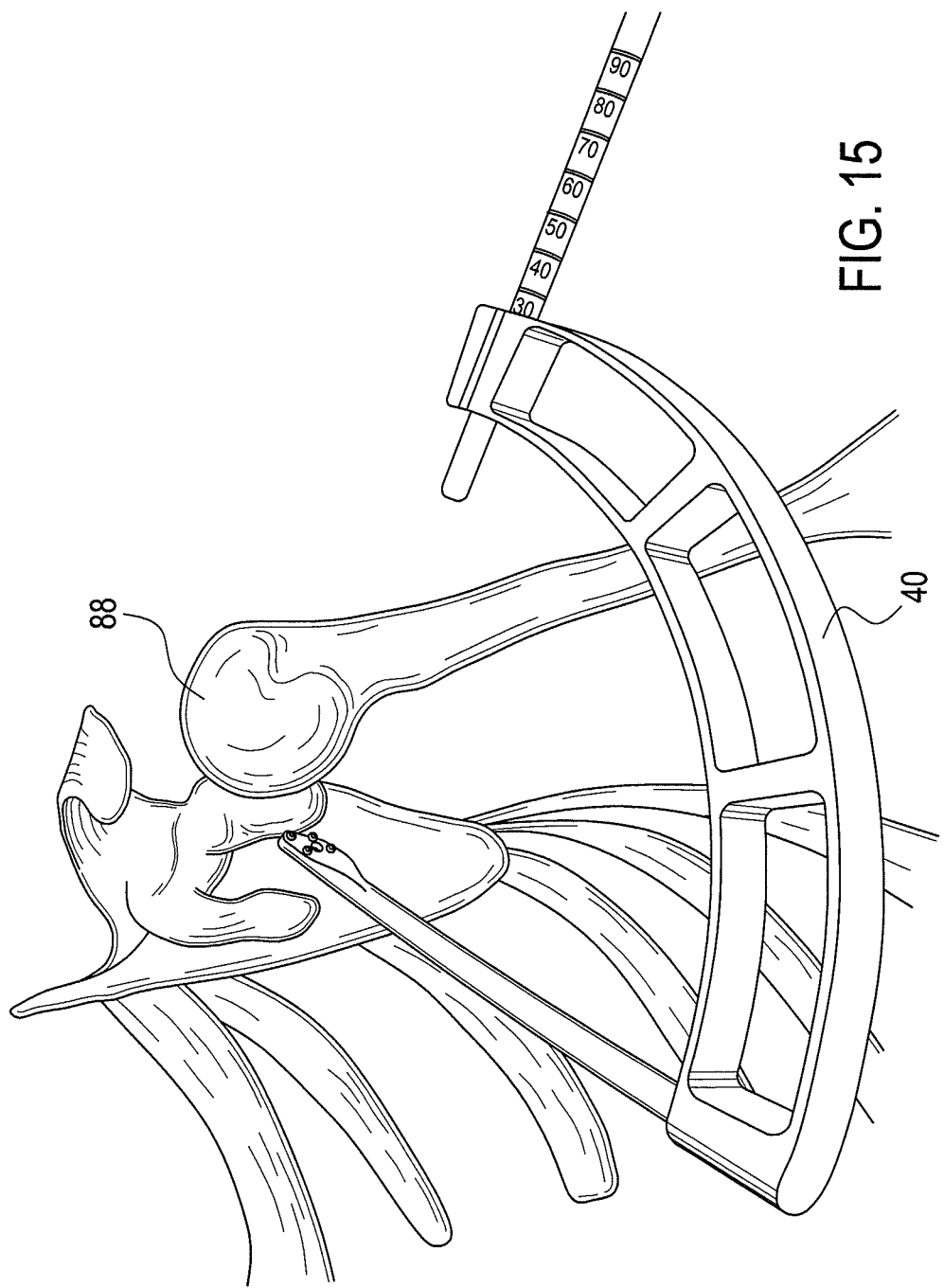
Figure 16:
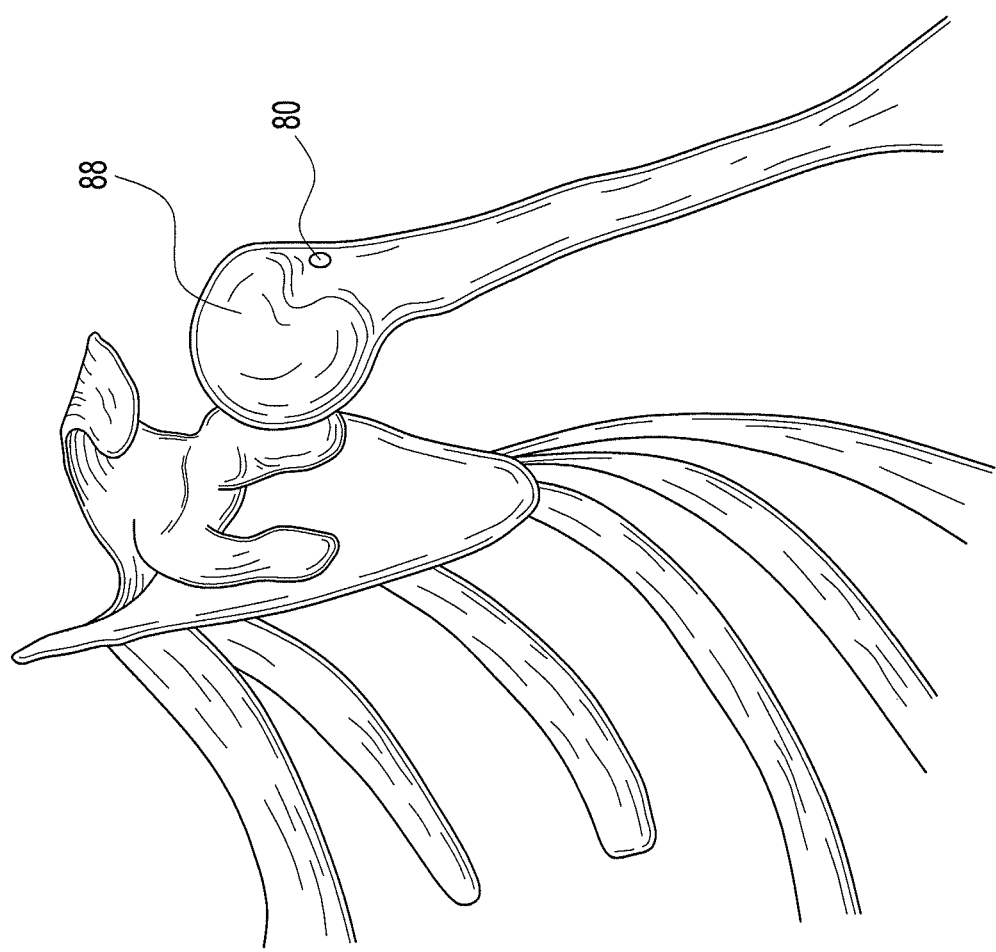
Figure 17:
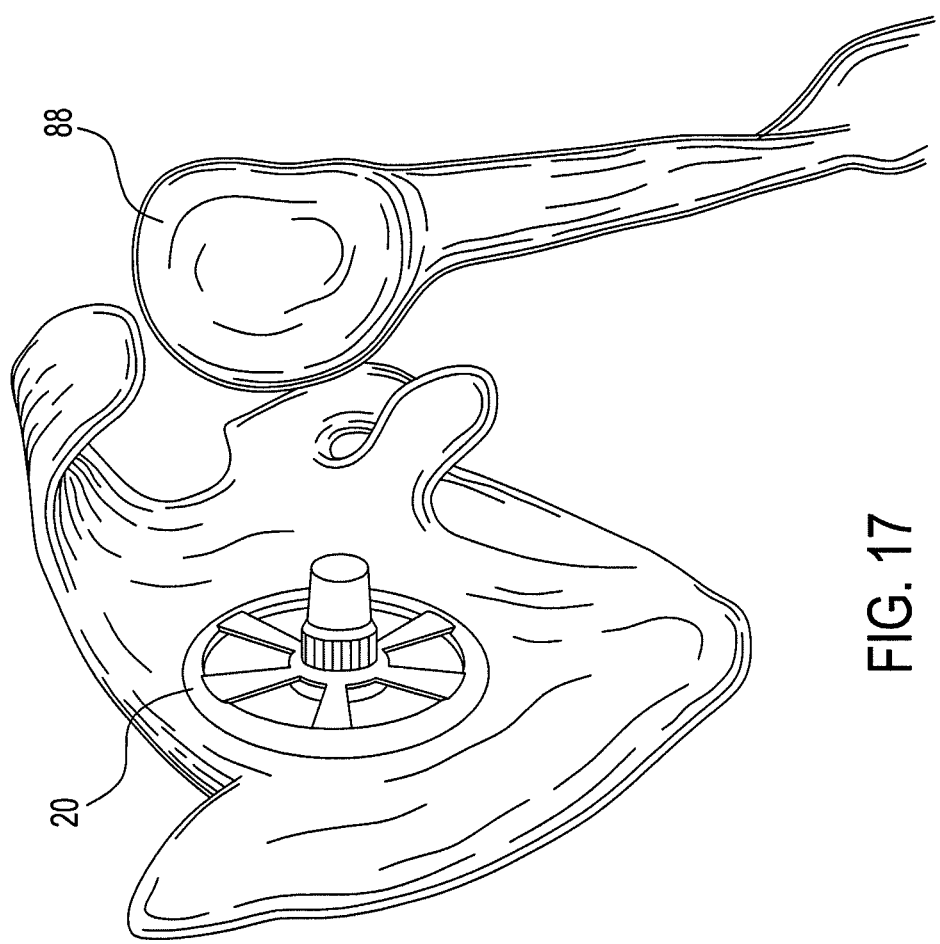

Specific steps of an exemplary method of humeral repair according to the present invention are detailed below and with reference to FIGS. 15-21 (which depict a method of replacing a portion of the humeral head with the partial humeral head prosthesis 10 of the present invention):

Use drill guide 40 with orthogonal orientation features to place 2.4 mm drill pin thru humeral head 88, exiting at center of focal defect (FIG. 15).

Remove drill guide 40, leaving the 2.4 mm drill pin in place.

Over-drill with 4 mm cannulated drill over 2.4 mm drill pin to form tunnel or hole 80 (FIG. 16) through the humerus 88, remove 4 mm drill leaving 2.4 mm drill pin in place.

Place sleeve component 50 over 2.4 mm drill pin, verifying whether sleeve 50 is in view with arthroscope. Remove 2.4 mm drill pin.

Insert threaded pin component 60 up sleeve 50 into view of arthroscope. Bring duster component 20 (FIG. 17), loaded onto insertion hand instrument, through rotator cuff interval portal into view. Assemble duster 20 to threaded pin 60 by hand.

Figure 18:
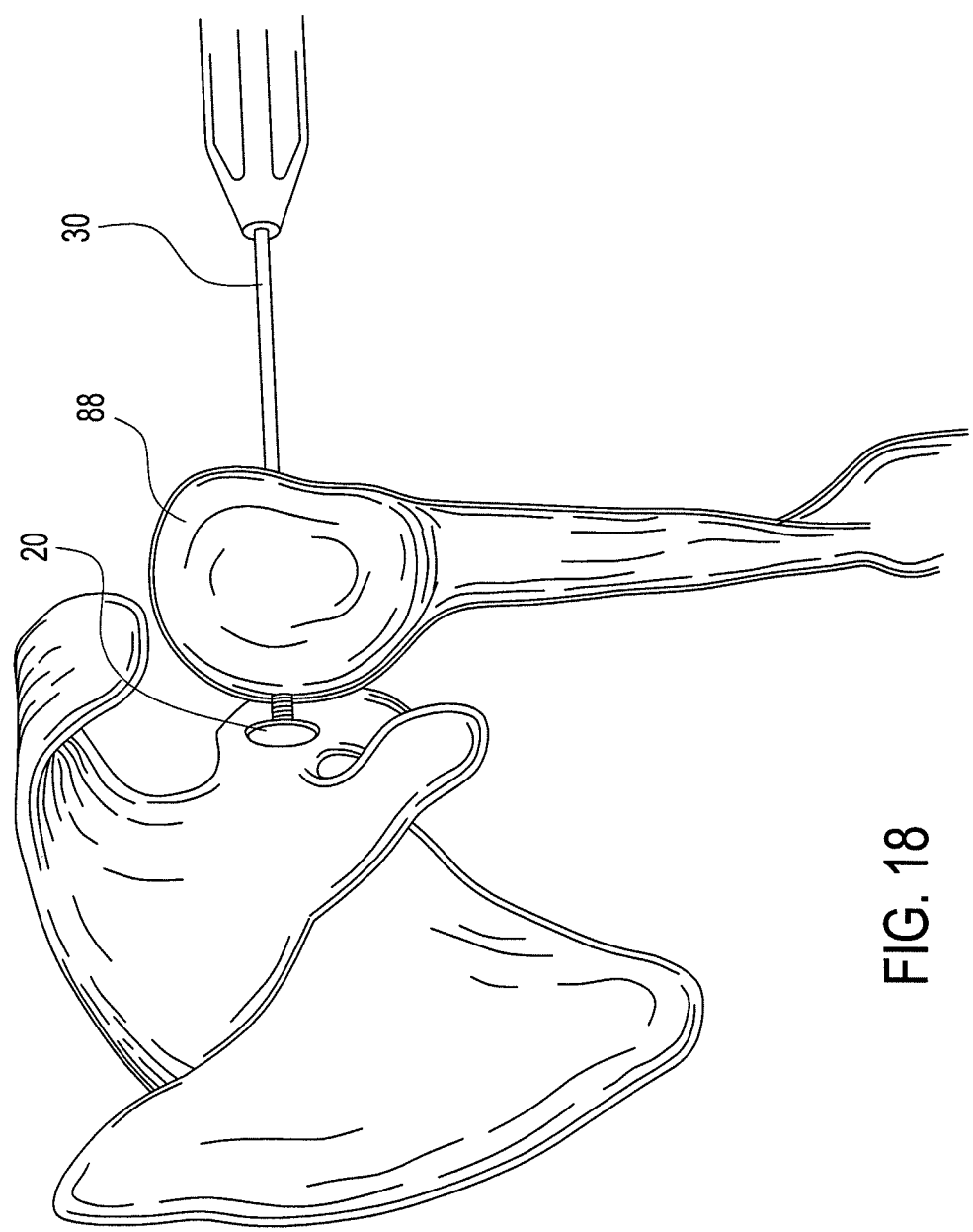

Load power drill onto threaded pin 60 and apply retrograde force while running drill to create a counterbore socket at focal defect location (FIG. 18).

Remove power drill. Grasp duster component 20 with insertion hand instrument and remove threaded pin 60, then remove duster component 20. Sleeve 50 should still be in place.

Figure 19:
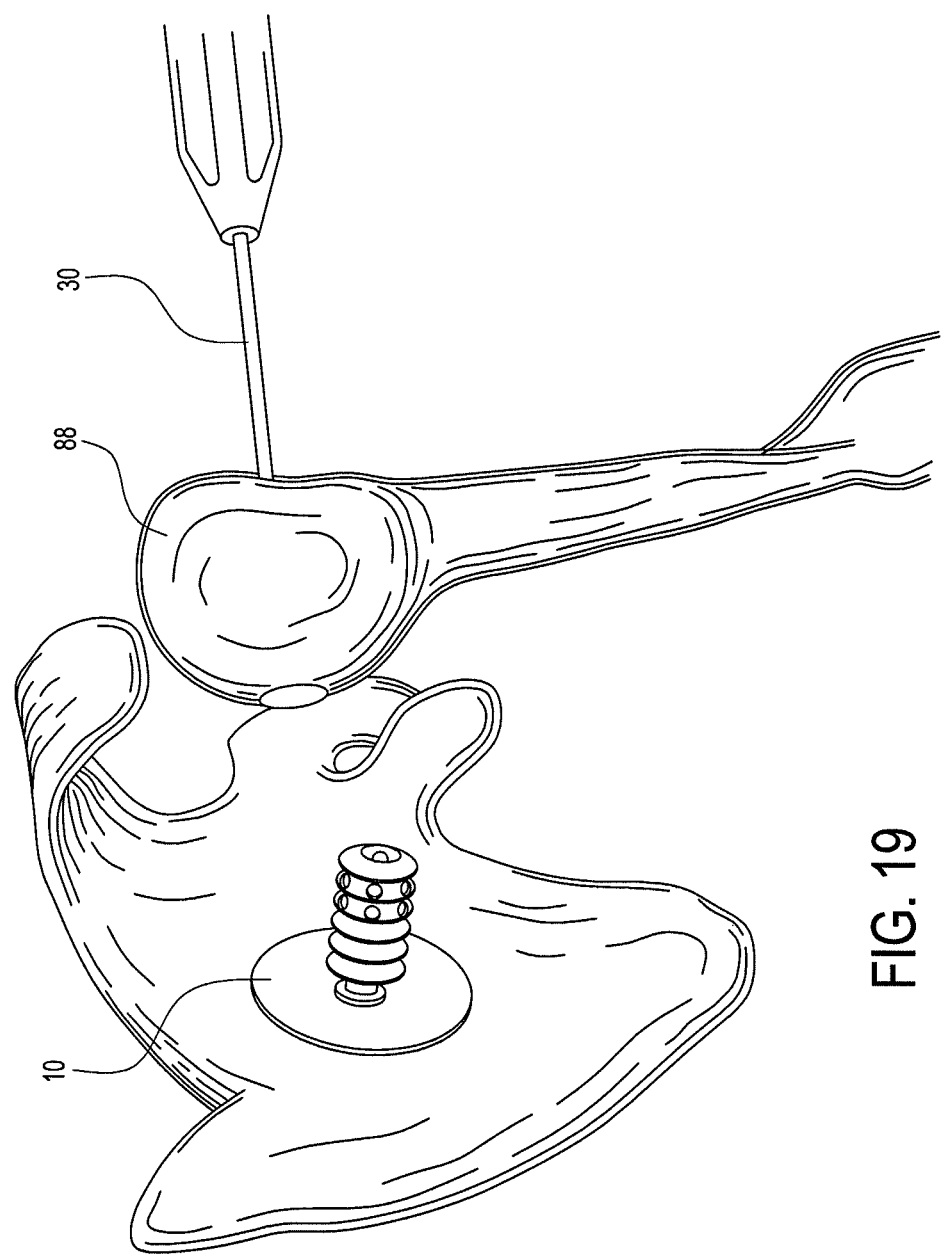

Insert implant inserter component 10 up sleeve into view of arthroscope. Bring implant 10, loaded onto insertion hand instrument, thru the rotator cuff interval portal into view (FIG. 19). Assemble implant 10 on inserter by hand.

Figure 20:
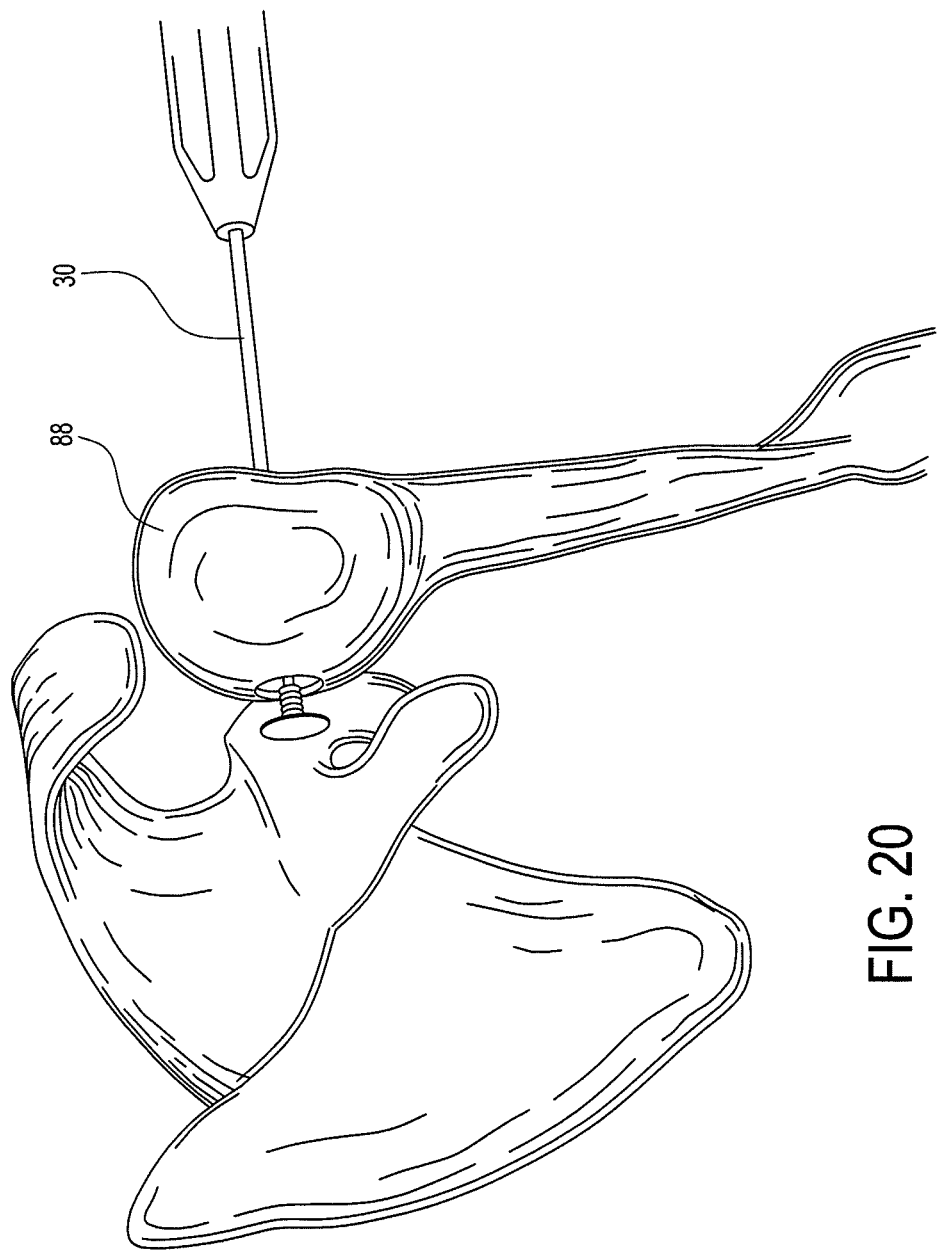

Retrograde insert implant 10 into the prepared socket until cap 4 of implant 10 is flush with the surrounding articular surface of the humerus (FIG. 20).

Remove the inserter, remove sleeve 50 and confirm that implant 10 is correctly installed (FIG. 21).

FIGS. 22 and 23 illustrate front and perspective views, respectively, of additional embodiments of a partial humeral head prosthesis 100(a), 100(b) formed according to a second embodiment of the present invention. Partial humeral head prosthesis 100(a), 100(b) is similar to the partial humeral head prosthesis 10 described above, but differs in that humeral head prosthesis 100(a), 100(b) is formed as a unitary structure rather than as an assembled structure (i.e., a partial humeral head prosthesis cap is integral to a partial implant or screw, and not assembled to it). Partial humeral head prosthesis 100(a), 100(b) comprises a partial humeral head prosthesis cap 104(a), 104(b) securely attached to, and integral with, a partial implant or screw 102(a), 102(b).

As shown in FIGS. 22 and 23, prosthesis cap 104(a), 104(b) is configured to allow replacement of a portion of the humeral head with the prosthesis cap. As in the previously-described embodiment, partial humeral head prosthesis cap 104(a), 104(b) has a convex configuration (a partial eclipse-type configuration), which is similar to the curvature of the humeral head to allow the prosthesis cap to reconstruct the anatomy of the damaged humeral head. The convex outer surface of the prosthesis cap 104(a), 104(b) permits both the full anatomical reconstruction of the humeral head and the introduction of the convex surface within the glenoid cavity. The concave, inner surface abuts the surface of the damaged articular bone to be replaced (i.e., portion of the humerus) and permits containment of any fractured, damaged humeral head. The dimension and measurements of the partial humeral head prosthesis cap 104(a), 104(b) are a function of the patient's anatomy.

Engagement element (neck portion) 101(a), 101(b) is provided between the partial humeral head prosthesis implant or screw 102(a), 102(b) and the prosthesis cap 104(a), 104(b). Implant or screw 102(a), 102(b) is provided with threads 108(a), 108(b) to allow the insertion and subsequent fixation of the screw (with prosthesis cap attached thereto) into the humerus diaphyseal channel. As shown in FIGS. 22 and 23, the length of the implant 102(a), 102(b) varies according to the length of the diaphyseal channel of the humerus.

A plurality of fenestrations or holes 106(a), 106(b) are formed through the body of the screw 102(a), 102(b) to permit the passage of any fixing material (such as acrylic cement, for example) through the walls of the screw, to increase the fixation of the device within the diaphyseal channel. The number of the fenestrations or holes 106(a), 106(b) depends on the length of the implant 102(a), 102(b) and also on the length of the diaphyseal channel of the humerus.

Partial humeral head prosthesis 100(a), 100(b) may be manufactured from titanium alloy or other metallic materials. The partial humeral head prosthesis cap 104(a), 104(b) preferably is manufactured from materials similar to those of the screw 102(a), 102(b).

Methods of conducting arthroscopic surgery by fixating the humeral head prosthesis 100(a), 100(b) within a socket in the humerus may be conducted by steps similar to those described and illustrated above with reference to humeral head prosthesis 10 of the first embodiment (for the humeral repair illustrated in FIGS. 15-21). Selection of the appropriate size for the partial humeral head prosthesis (implant) 100(a), 100(b) is based on the patient's anatomical requirements. The specific steps proceed as detailed above and with reference to FIGS. 15-21.

FIGS. 24a, 24b and 24c illustrate different views of humeral head prosthesis 110 formed according to a third embodiment.

Humeral head prosthesis 110 is similar to partial humeral head prosthesis 10 described above, but differs significantly in that humeral head prosthesis 110 may articulate.

Humeral head prosthesis 110 includes cap 112, screw 120, socket 130, articulating part 140 and spacer 150 as illustrated in FIG. 24a. Cap 112 includes inner surface 113, convex outer surface 114, receptacle 116 and helical grooves 118.

Screw 120 is cannulated in shape and includes fenestrations or holes 122, humerus threads 124 and attachment threads 126. Screw 120 is provided with threads 124 to allow the insertion and subsequent fixation of screw 120 (with prosthesis cap 112 attached thereto) into the humerus diaphyseal channel. A plurality of fenestrations or holes 112 formed through the body of screw 120 permit the passage of any fixing material (such as acrylic cement, for example) through the walls of screw 120, to increase the fixation of humeral head prosthesis 110 within the diaphyseal channel.

Socket 130 is defined by outside surface 131 between proximal end 134 and distal end 136. Outside surface 131 is cylindrical in shape and has attachment threads 133 extending between proximal end 134 and distal end 136. Socket 130 includes inside surface 132 that has a frustoconical shape tapering from proximal end 134 to distal end 136. Socket 130 also has socket opening 138 having a circular cross section located at distal end 136. Opening 138 extends from distal end 136 to inside surface 132 and has a cylindrical shape.

Articulating part 140 has a frustoconical shape that tapers from proximal end 144 to distal end 146. Part 140 includes bore 142 that extends partially through part 140 from distal end 146 toward proximal end 144 and has helical grooves 143 along the surface of bore 142. In another embodiment, bore 142 extends through articulating part 140 from distal end 146 to proximal end 144.

Spacer 150 is cylindrical in shape and includes outer spacer surface 152 and inner spacer surface 154. Inner spacer surface 154 has a concave shape. Spacer 150 further includes circular opening 156, centered in the middle of spacer 150. In another embodiment, inner spacer surface 154 is flat or has a convex shape.

As shown in FIGS. 24b and 24c, humeral head prosthesis 110 is formed by placing articulating part 140 within socket 130 so that the outside surface of articulating part 140 contacts inside surface 132 of socket 130. Further, bore 142 aligns with socket opening 138 to allow access to bore 142 through socket opening 138. Socket 130 is attached to cap 112. Socket 130 is housed within receptacle 116 of cap 112 and attachment threads 133 of socket 130 align and mate with helical grooves 118 of cap 112 to secure socket 130 within receptacle 116. Spacer 150 is attached to cap 112, with outer spacer surface 152 contacting inner surface 113 of cap 112.

In another embodiment, spacer 150 is not part of humeral head prosthesis 150 and inner surface 113 abuts the surface of the damaged articular bone. In this embodiment, inner surface 113 may be concave or convex.

Bore 142 of articulating part 140 houses attachment threads 126 of screw 120. Attachment threads 126 mate with helical grooves 143 of bore 142 to secure screw 120 to articulating part 140. Screw 120 extends through spacer opening 156 and socket opening 138 and away from cap 112.

In another embodiment, prosthesis cap 112 is attached to the humeral bone without the use of screw 120. In this embodiment a through-bolt is used to attach prosthesis cap 112 to the humeral bone. The through-bolt extends from one side of the humeral bone, through the humerus diaphyseal channel and attaches to prosthesis cap 112. The through-bolt may have threads similar to screw 120 to mate with helical grooves 143 to secure the through-bolt to articulating part 140. In this manner, the through-bolt securely seats prosthesis cap 112 on the humeral head. Other methods known in the art for seating prosthesis cap 112 on humeral bone may be employed without deviating from the inventive concept described in the present application.

The above described configuration of humeral head prosthesis 110 allows articulation or movement of cap 112 with respect to screw 120. Cap 112 may freely articulate in any direction between 0° and 30° off centerline axis, wherein the centerline axis typically aligns with the perpendicular of screw 120. This movement is provided by articulating part 140 and socket 130. Articulating part 140 and socket 130 act as a ball and socket joint respectively, allowing articulating part 140 to move along inside surface 132 of socket 130. This articulation allows cap 112 to be self-centering and enhances the seating of cap 112 on the humeral bone.

As in previously-described embodiments, the convex configuration (a partial eclipse-type configuration) of humeral head prosthesis cap 112 is similar to the curvature of the humeral head to allow prosthesis cap 112 to reconstruct the anatomy of the damaged humeral head. Convex outer surface 114 of prosthesis cap 112 permits both the full anatomical reconstruction of the humeral head and the introduction of convex surface 114 within the glenoid cavity. Concave inner surface 154 of spacer 150 abuts the surface of the damaged articular bone to be replaced (i.e., portion of the humerus) and permits containment of any fractured, damaged humeral head. The dimension and measurements of humeral head prosthesis cap 112 is a function of the patient's anatomy.

As described in this embodiment, prosthesis cap 112 may be used as a complete prosthesis or as a partial prosthesis to treat focal defects in the humeral bone. Prosthesis cap 112 may also be used to treat osteoarthritis in the humeral bone as well as other medical conditions. The uses of prosthesis cap 112 should not be limited to the above mentioned conditions, but may have a variety of different uses. Further, prosthesis cap 112 may also be used to treat medical conditions in other bones besides the humeral bone.

Humeral head prosthesis cap 112 may be manufactured from titanium alloy or other metallic materials. Humeral head prosthesis cap 112 is preferably manufactured from materials similar to those of screw 120.

FIGS. 25a, 25b and 25c illustrate different views of reamer assembly 200 formed according to a third embodiment.

Reamer assembly 200 is similar to partial humeral head prosthesis duster 20 described above, but differs in many respects, one being that reamer assembly 200 may articulate.

Reamer assembly 200 includes reamer 210, drive pivot 220 and retaining cap 230 as illustrated in FIG. 25a. Reamer 210 has a circular cross section, similar to humerus head prosthesis 110. Reamer 210 includes three cutting edges 216, 217 and 218 that are equally spaced at 120° intervals around reamer 210. Cutting edges 216, 217 and 218 extended from the outside surface of reamer 210 toward middle of reamer 210. In another embodiment, cutting edges 216, 217 and 218 are not equally spaced around reamer 210.

Reamer 210 further includes cylindrical socket 214. Socket 214 includes frustoconical shaped indentation 215 centered in the middle of socket 214 and extending away from reamer face 211. Reamer 210 further includes slots 212 and 213 that are equally spaced along the outside wall of socket 214. Slots 212 and 213 create openings between the outside wall of socket 214 and indentation 215. Further, slots 212 and 213 are "U" shaped, extending away from reamer face 211 with an opening toward reamer face 211. Slots 212 and 213 do not extend the total depth of socket 214.

Drive pivot 220 has a frustoconical shape, tapering from proximal end 228 to distal end 226. Further, drive pivot 220 includes bore 228 that has a cylindrical shape. Bore 228 extends from proximal end 228 toward distal end 226 but does not extend completely too distal end 226. Bore 226 also has helical grooves 229 along its surface. Drive pivot 220 includes cylindrical arms 222 and 224 that extend perpendicularly away from drive pivot 220. Retaining cap 230 is circular and includes opening 232 at the center of retaining cap 230.

As illustrated in FIGS. 25b and 25c, reamer assembly 200 is formed by placing drive pivot 220 within indentation 215 of socket 214. Arms 222 and 224 of drive pivot 220 extended through slots 212 and 213 of socket 214. Retaining cap 230 covers socket 214 and drive pivot 220, with opening 232 of retaining cap 230 aligned with bore 228 of drive pivot 220. Threaded pin 60 extends through retaining cap 230 and mate with helical grooves 229 of bore 228.

In another embodiment, bore 228 does not have helical grooves 229, but contains a pin extending from one side of bore 228 to another. Threaded pin 60 includes a slot at one end that engages with reamer assembly 200. In use, threaded pin 60 extends through retaining cap 230 and the end of threaded pin 60 that contains the slot enters bore 228. The pin within bore 228 is sized to allow it to rest within the slot of threaded pin 60. In this manner, threaded pin 60 may engage and exert a torque on reamer assembly 200.

In operation, threaded pin 60 is rotated and exerts a torque on drive pivot 220. Arms 222 and 224 of drive pivot 220 subsequently exert a force on the sides of slots 218 and 219, causing reamer assembly 200 to rotate. In this embodiment, reamer 200 may be drilled in a retrograde manner.

With arms 222 and 224 extending through slots 212 and 213 and drive pivot 220 located within indentation 215, reamer driver 210 may articulate in any direction from 0° to 30° off centerline axis. Typically, the centerline axis aligns with the perpendicular of threaded pin 60.

In another embodiment, socket 214 includes a bore that extends away from reamer face 211. The bore extends from the bottom of indentation 215 to the side of socket 214 opposite reamer face 211. In this embodiment, threaded pin 60 pass through the bore and mates with helical grooves 229 of drive pin 220. Accordingly, reamer 200 may be drilled in a forward antegrade manner.

FIGS. 26a, 26b and 26c illustrate reamer grasper 300. FIG. 26a shows reamer grasper 300 that includes grasper tip 310, tube 320, actuator 330, washer 332, wishbone spring 334, handles pins 336 and 338, wishbone thumb 340, wishbone finger 342, wishbone lock 358 and wishbone lock pins 352, 354, and 356.

FIG. 26b shows grasper tip 310, grasper tip 310 includes tube 312, cutter pin 314, tip pin 316 and grasper jaw 318. Reamer grasper 300 is used in surgery to grasp reamer assembly 200.

FIGS. 27a, 27b and 27c illustrate implant grasper 400. FIG. 26a shows implant grasper 400 that includes grasper tip 410, tube 420, actuator 430, washer 432, wishbone spring 434, handles pins 436 and 438, wishbone thumb 440, wishbone finger 442, wishbone lock 458 and wishbone lock pins 452, 454, and 456.

FIG. 27b shows grasper tip 410, grasper tip 410 includes tube 412, cutter pin 414, tip pin 416 and grasper jaw 418. Implant grasper 400 is used in surgery to grasp humeral head prosthesis 110.

A method of conducting arthroscopic surgery by fixating humeral head prosthesis 110 of the present embodiment within a socket in the humerus is now described. Preparation for an exemplary surgical technique relies upon radiographic film, surgical templates, and trial implants to determine and select the appropriate combination of prosthesis cap 112 and screw 120 that make up humeral head prosthesis 110 to meet the patient's anatomical requirements. The remaining fractured/damaged humerus is resected using appropriate instrumentation designed specifically for the implant system.

Specific steps of a method of humeral repair are detailed below with reference to FIGS. 28-34 (which depict a method of replacing a portion of the humeral head with humeral head prosthesis 110):

Step 1

After the focal chondral defect is identified on the humeral articular surface, a small anterior incision is made. FIG. 28 shows guide 40 (for example, a C-Ring guide) inserted through the anterior incision and rotator interval. The C-Ring guide cup is placed over the chondral defect so that it covers the entire defect and sits flush on the articular surface. C-Ring guide drill sleeve 50 is pushed against the skin of the lateral shoulder. At that location, a skin incision is made and the soft tissue is bluntly dissected down to bone taking care to avoid the axillary nerve. C-Ring guide drill sleeve 50 is further inserted into the wound, until it makes contact with bone. Care must be taken to avoid the axillary nerve when inserting drill sleeve 50.

Step 2

A guide pin (such as a 2.4 mm guide pin) is inserted into drill sleeve 50 and the pin is drilled through humerus head 88 until it exits the humeral articular surface. The pin is detached from the drill and left in place. The C-Ring guide 40 is now removed completely or left in place to act as a drill stop. Next, a soft tissue protector is placed over the 2.4 mm guide pin. A 4 mm cannulated drill is placed over the 2.4 mm guide pin and through the soft tissue protector. It is then drilled through the lateral humerus until it exits the articular surface. FIG. 29 shows tunnel or hole 80 through humerus head 88 made by the 4 mm cannulated drill. The 4 mm cannulated drill, C-Ring guide 40, and the soft tissue protector are removed and the 2.4 mm guide pin is left in place. A transhumeral tunnel sleeve is placed over the guide pin and through the previously drilled 4 mm tunnel 80 until it is flush with the articular surface. The guide pin is now removed.

Step 3

Figure 30:
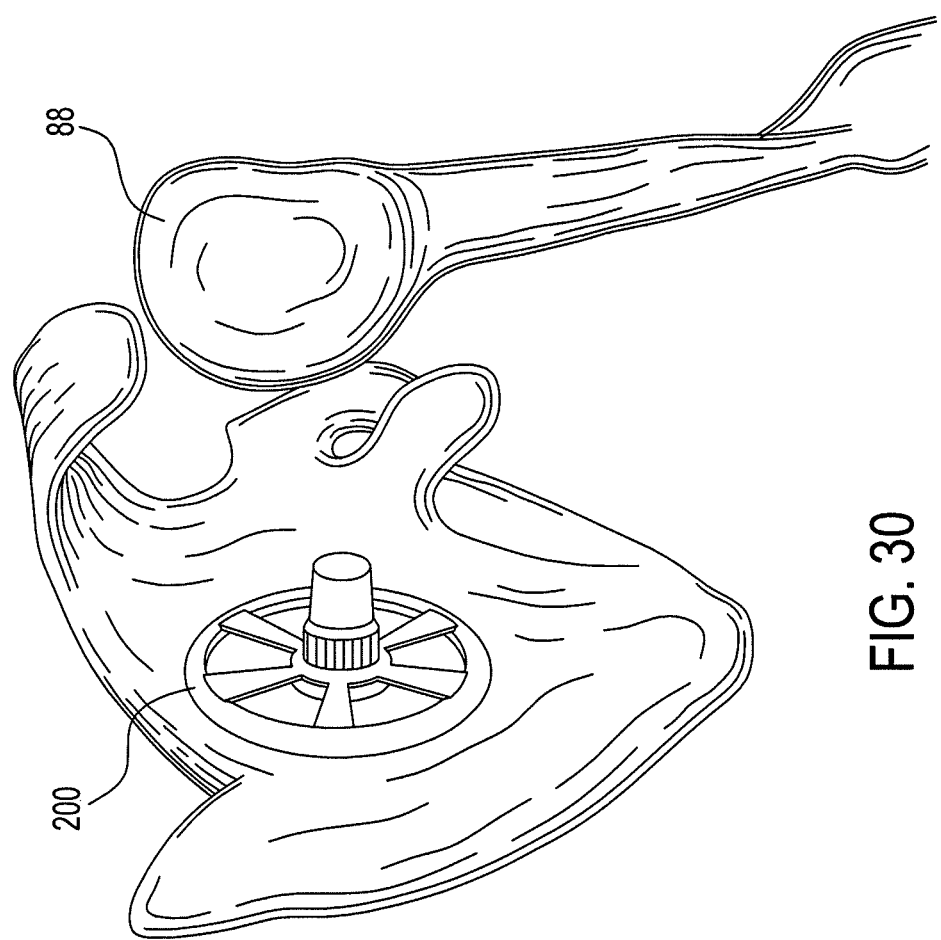
Figure 31:
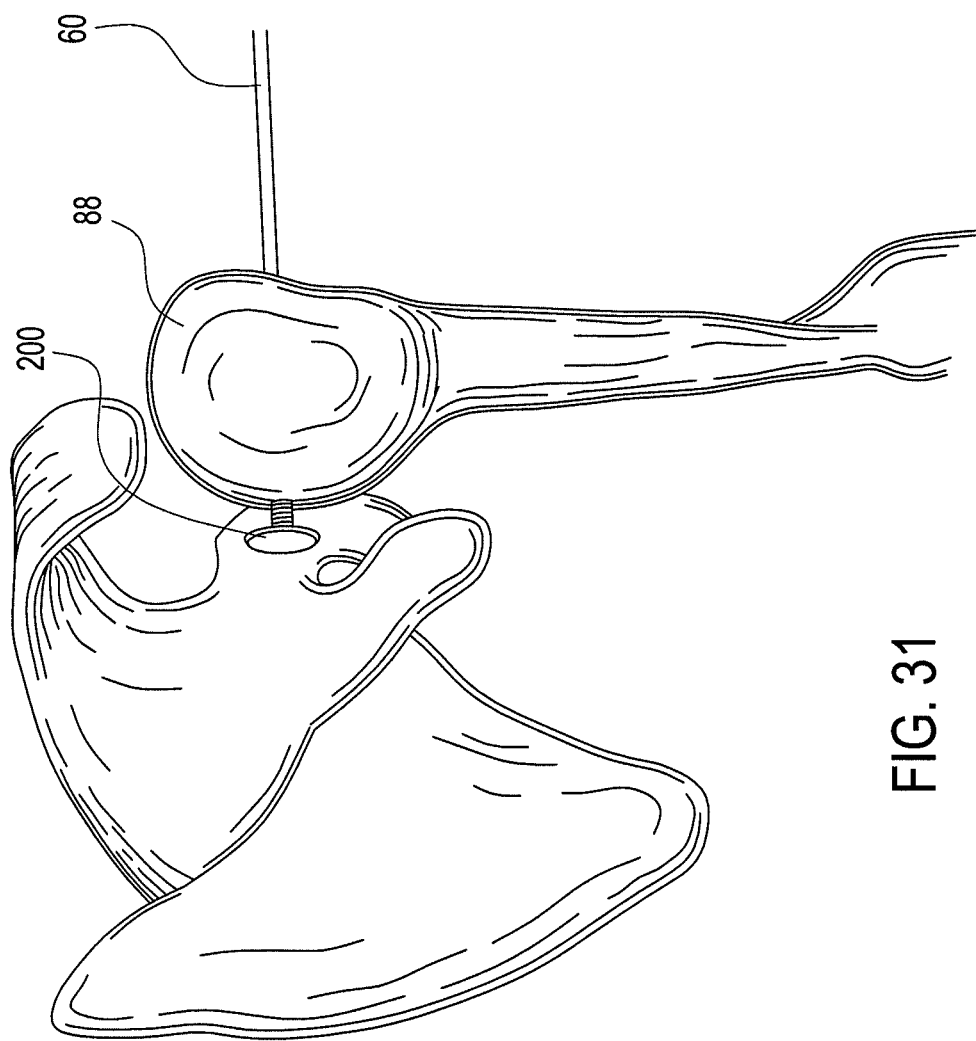

In FIG. 30, the appropriate size reamer 200 is connected to reamer grasper 300 and inserted through the anterior shoulder incision and rotator interval. Threaded pin 60 is attached to a handled chuck and inserted through the transhumeral tunnel sleeve and into the intraarticular space. In FIG. 31, reamer grasper 300 is used to manipulate reamer 200 into place and mate it with threaded pin 60. Once connection of reamer 200 and threaded pin 60 is confirmed, the handled chuck is removed and threaded pin 60 is connected to power. Reamer grasper 300 is disengaged and the articular surface is reamed until the reamer depth stop ring fully contacts humeral head 88 to create reamed articular region 95. The power drill is now disconnected. Reamer grasper 300 and handled chuck are used to disengage reamer 200 from threaded pin 60 and both items are removed from the intraarticular space.

Step 4

Figure 32:
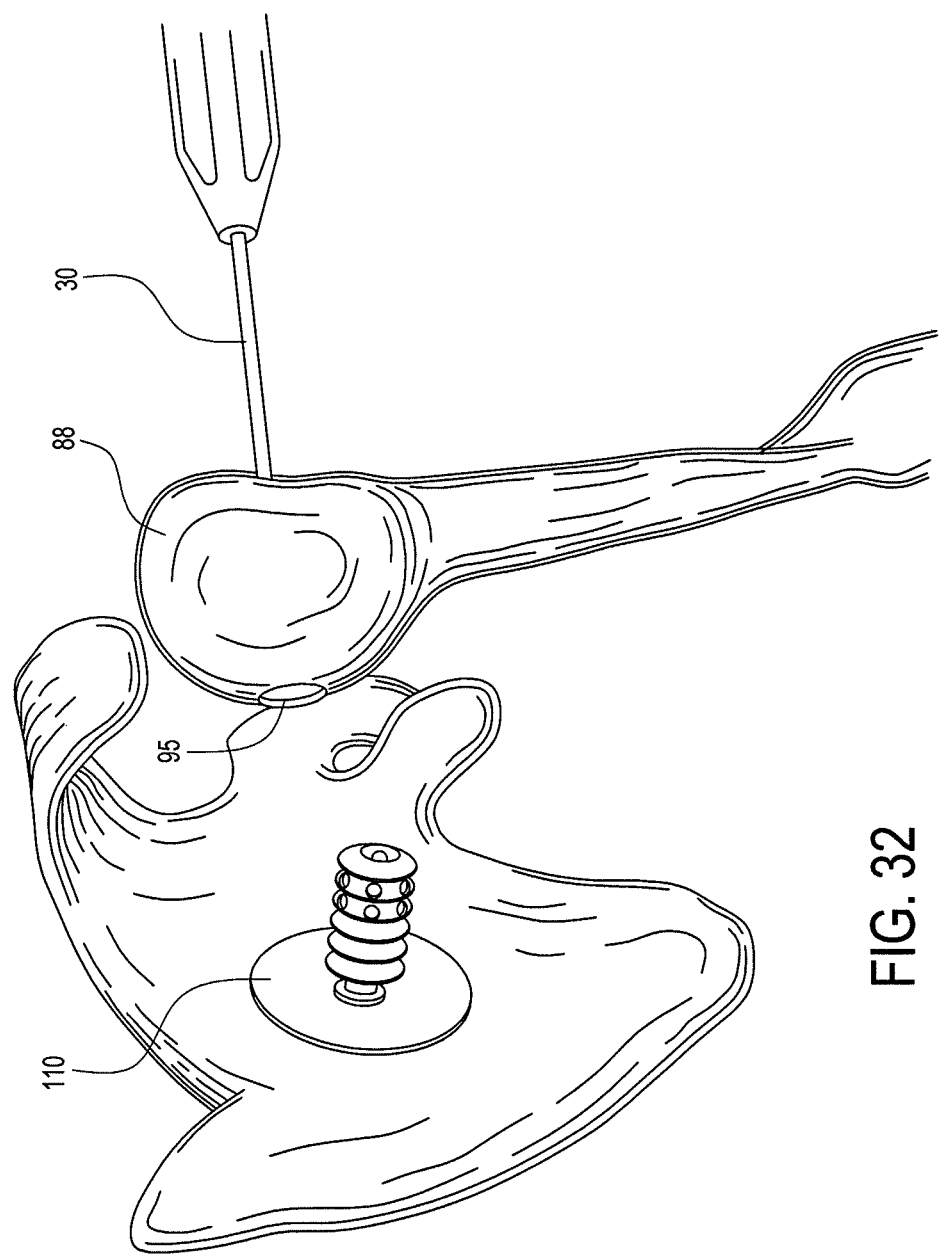
Figure 33:
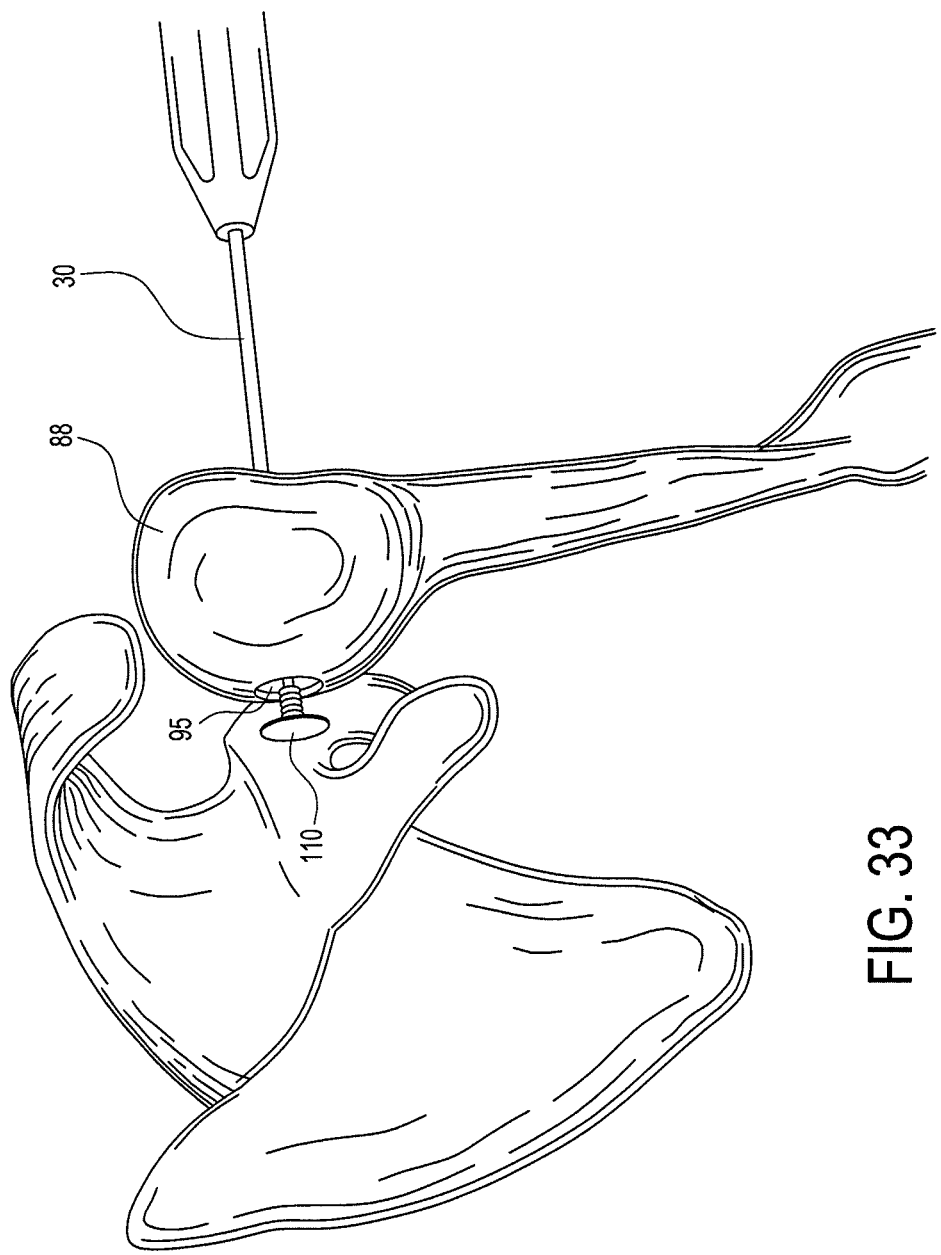
Figure 34:
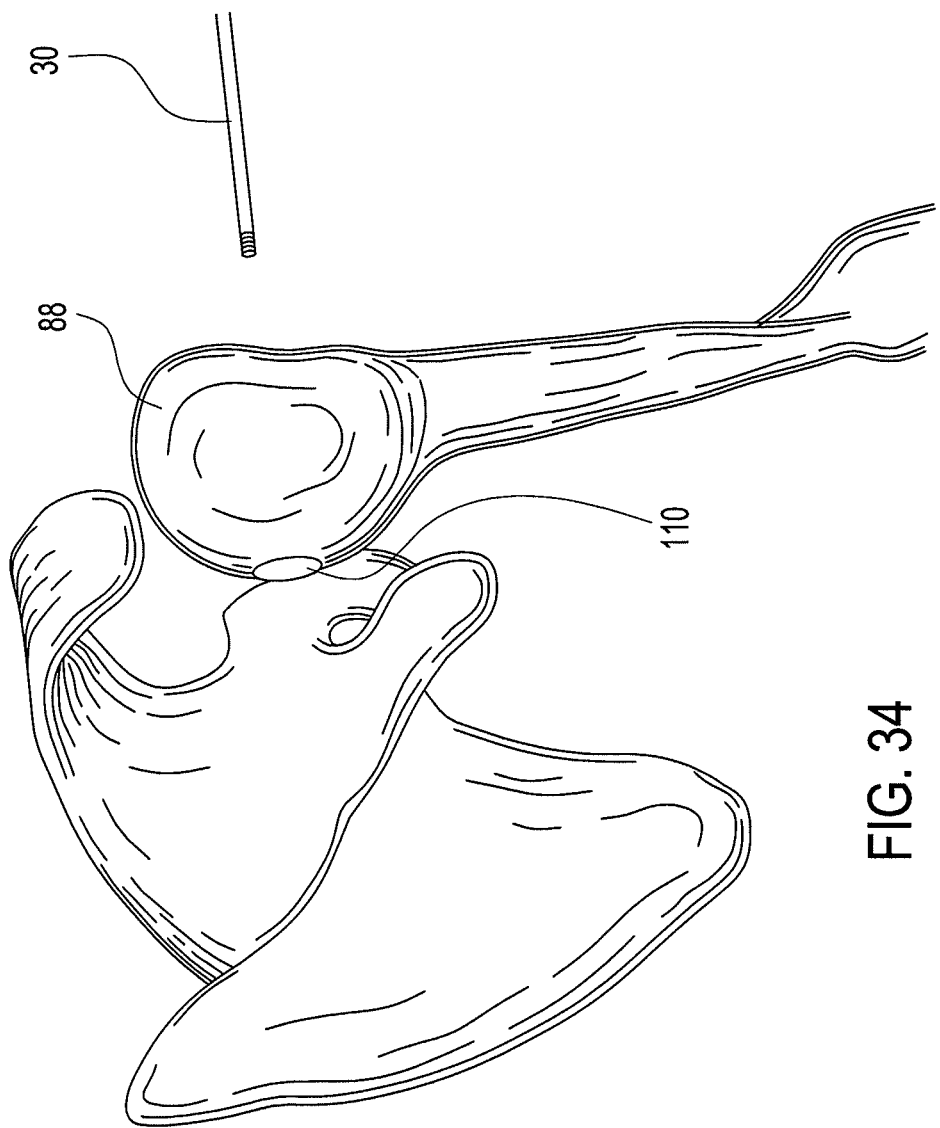

In FIG. 32, implant grasper 400 is used to insert the appropriate size humeral head prosthesis 110 through the anterior shoulder incision and rotator interval. Implant driver 30 is inserted through the transhumeral tunnel sleeve and connected to humeral head prosthesis 110 within the intraarticular space. In FIG. 33, Humeral head prosthesis 110 is driven into reamed articular region 95 in a retrograde fashion using implant driver 30. In FIG. 34, after complete seating of humeral head prosthesis 110 is confirmed, implant 30 driver is disengaged and removed. Lastly, the transhumeral tunnel sleeve is removed.

FIGS. 35a, 35b and 35c illustrate humeral head prosthesis 110 seated on humeral head 88 after completion of the above described method. FIG. 35a illustrates humeral head prosthesis 110 in a neutral non-articulated position. Prosthesis cap 112 is perpendicular to screw 120 and no articulation is necessary for prosthesis cap 112 to seat correctly on humeral head 88 since the initial drilling pin exited the surface of the bone at exactly a perpendicular angle.

FIGS. 35b and 35c illustrates humeral head prosthesis 110 in an off axis articulated position. Prosthesis cap 112 is articulated or tilted with regard to the perpendicular of screw 130. This articulation allows prosthesis cap 112 to be correctly seated on humeral head 88. If prosthesis cap 112 could not articulate, prosthesis cap 112 might not be correctly seated on humeral head 88, leaving a gap between humeral head 88 and prosthesis cap 112.

As described and shown in FIGS. 24-35, humeral head prosthesis 110 and reamer assembly 200 allow for slight errors in the placement of the initial drilling pin during the method described above. If the initial drilling pin does not exit the surface of humeral head 88 at exactly a perpendicular angle, prosthesis 110 and reamer 200 may articulate to compensate for the drilling error, allowing for complete seating of prosthesis 110 on humeral head 88.

The above description and drawings illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed as new and desired to be protected by Letters Patent of the United States is:

1. A method of shoulder repair, the method comprising the steps of:
providing a humeral prosthetic, comprising:
a cannulated screw having a proximal end and a distal end, the cannulated screw being provided with threads to allow insertion and fixation of the cannulated screw into a humeral diaphyseal channel, the cannulated screw being further provided with a threaded region with attachment threads at its proximal end; a head secured to the proximal end of the cannulated screw, the head having a convex surface suitable to be introduced within a joint cavity, the head being provided with a receptacle with helical grooves;
a spacer attached to the head so that an outer spacer surface contacts an inner surface of the head;
an articulating coupling element attaching the cannulated screw to the head to form an articulating joint, wherein the articulating joint allows the head to articulate in relationship to the cannulated screw, wherein the articulating coupling element is an articulating part with an outer surface having a tapered frustoconical shape and comprising a threaded bore, the threaded bore receiving the attachment threads of the cannulated screw to secure the head to the cannulated screw; and
a socket disposed between the head and to the articulating part, so that an inside surface of the socket has a tapered frustoconical shape to allow the articulating coupling element to be placed within the socket so that the outer surface of the articulating coupling element contacts an inside surface of the socket, and so that the outer surface of the articulating part moves along the inside surface of the socket and allows the head to be self-centering and to be seated correctly on a humerus, wherein an outer surface of the socket is provided with attachment threads that align and mate with the helical grooves of the head receptacle;

preparing a bone socket in the humerus by drilling a pin through a humerus head until the pin exits a humeral articular surface, wherein the step of preparing the bone socket further comprises using an articulating reamer assembly that comprises an articulating joint and a reamer driver with a plurality of cutting edges, the articulating joint connecting to the reamer driver and further comprising a drive pivot that engages a circular retaining cap and a socket, the circular retaining cap covering the socket and the drive pivot, and forming a reamed articulating region on the humerus head by connecting the articulating reamer assembly with the pin and connecting the pin to a power source;

connecting an implant driver to the humeral prosthetic and within an intraarticular space of the shoulder joint by attaching the cannulated screw with the head, the socket and the articulating coupling element to the implant driver inside the joint cavity, the implant driver being inserted into the joint cavity through a preformed tunnel in the humerus, and installing the prosthetic, in retrograde fashion, into the humerus, using the implant driver;

driving the humeral prosthetic into the reamed region on the humerus head in a retrograde manner using the implant driver until the convex surface of the head is flush with a contour of the humerus; and seating the humeral prosthetic on the humeral head and in the bone socket so that the articulating coupling element interacts with the socket of the humeral prosthetic to form an articulating ball and socket joint so that the outer surface of the articulating part moves along the inside surface of the socket and allows the head to be self-centering and to be seated correctly on a humerus, allowing the head to articulate in off axis articulated or titled positions relative to the cannulated screw, and wherein the head of the humeral prosthetic is seated correctly on the humeral surface even when the pin does not exit the humeral articular surface at exactly a perpendicular angle, and wherein the head of the humeral prosthetic articulates to compensate for any drilling error.

2. The method of claim 1, further comprising:
resecting a portion of the humeral head at a defect location;
preparing the bone socket in the defect location of the humerus; and
attaching the head of the prosthetic to the humeral head in the bone socket at the defect location so that the head of the prosthetic is flush with the humeral contour.

3. The method of claim 1, wherein the head articulates in any direction from 0° to 30° off a centerline axis which aligns with a perpendicular of the cannulated screw, and in relationship to the cannulated screw.

4. The method of claim 1, wherein the cannulated screw includes a plurality of fenestrations.

* * * * *